United States Patent
Naga et al.

(10) Patent No.: US 10,182,865 B2
(45) Date of Patent: Jan. 22, 2019

(54) MICROWAVE CATHETER APPARATUSES, SYSTEMS, AND METHODS FOR RENAL NEUROMODULATION

(71) Applicant: Medtronic Ardian Luxembourg S.a.r.l., Luxembourg (LU)

(72) Inventors: Karun D. Naga, Los Altos, CA (US); Roman Turovskiy, San Francisco, CA (US); Denise Zarins, Saratoga, CA (US); Mark Gelfand, New York, NY (US); Arye Rosen, Cherry Hill, NJ (US)

(73) Assignee: Medtronic Ardian Luxembourg S.a.r.l., Luxembourg (LU)

( * ) Notice: Subject to any disclaimer, the term of this patent is extended or adjusted under 35 U.S.C. 154(b) by 0 days.

(21) Appl. No.: 15/261,732

(22) Filed: Sep. 9, 2016

(65) Prior Publication Data
US 2017/0007325 A1    Jan. 12, 2017

Related U.S. Application Data

(63) Continuation of application No. 13/281,244, filed on Oct. 25, 2011.
(Continued)

(51) Int. Cl.
*A61B 18/18*   (2006.01)
*A61B 18/00*   (2006.01)

(52) U.S. Cl.
CPC .. *A61B 18/1815* (2013.01); *A61B 2018/0022* (2013.01); *A61B 2018/00023* (2013.01);
(Continued)

(58) Field of Classification Search
None
See application file for complete search history.

(56) References Cited

U.S. PATENT DOCUMENTS

| | | |
|---|---|---|
| 4,602,624 A | 7/1986 | Naples et al. |
| 4,649,936 A | 3/1987 | Ungar et al. |

(Continued)

FOREIGN PATENT DOCUMENTS

| | | |
|---|---|---|
| CA | 2384866 | 4/2001 |
| CN | 101610735 | 12/2009 |

(Continued)

OTHER PUBLICATIONS

Allen, E.V., Sympathectomy for essential hypertension, Circulation, 1952, 6:131-140.
(Continued)

*Primary Examiner* — Kaitlyn Smith

(57) ABSTRACT

Microwave catheter apparatuses, systems, and methods for achieving renal neuromodulation by intravascular access are disclosed herein. One aspect of the present application, for example, is directed to apparatuses, systems, and methods that incorporate a catheter treatment device comprising an elongated shaft. The elongated shaft is sized and configured to deliver a microwave transmission element to a renal artery via an intravascular path. Renal neuromodulation may be achieved via dielectric heating in the presence of microwave irradiation that modulates neural fibers that contribute to renal function or alters vascular structures that feed or perfuse the neural fibers.

15 Claims, 17 Drawing Sheets

Related U.S. Application Data

(60) Provisional application No. 61/406,534, filed on Oct. 25, 2010.

(52) U.S. Cl.
CPC .............. *A61B 2018/00404* (2013.01); *A61B 2018/00434* (2013.01); *A61B 2018/00511* (2013.01); *A61B 2018/00577* (2013.01); *A61B 2018/00791* (2013.01); *A61B 2018/1861* (2013.01)

(56) References Cited

U.S. PATENT DOCUMENTS

| | | | |
|---|---|---|---|
| 4,709,698 A | 12/1987 | Johnston et al. | |
| 4,764,504 A | 8/1988 | Johnson et al. | |
| 4,799,479 A | 1/1989 | Spears | |
| 4,890,623 A | 1/1990 | Cook et al. | |
| 4,976,711 A | 12/1990 | Parins et al. | |
| 5,007,437 A | 4/1991 | Sterzer | |
| 5,019,075 A | 5/1991 | Spears et al. | |
| 5,057,106 A | 10/1991 | Kasevich et al. | |
| 5,129,396 A | 7/1992 | Rosen et al. | |
| 5,150,717 A | 9/1992 | Rosen et al. | |
| 5,191,883 A | 3/1993 | Lennox et al. | |
| 5,234,004 A | 8/1993 | Hascoet et al. | |
| 5,300,068 A | 4/1994 | Rosar et al. | |
| 5,300,099 A | 4/1994 | Rudie | |
| 5,314,466 A | 5/1994 | Stern et al. | |
| 5,330,518 A | 7/1994 | Neilson et al. | |
| 5,358,514 A | 10/1994 | Schulman et al. | |
| 5,364,392 A | 11/1994 | Warner et al. | |
| 5,368,591 A | 11/1994 | Lennox et al. | |
| 5,405,346 A | 4/1995 | Grundy et al. | |
| 5,423,744 A | 6/1995 | Gencheff et al. | |
| 5,464,445 A | 11/1995 | Rudie et al. | |
| 5,484,400 A | 1/1996 | Edwards et al. | |
| 5,540,679 A | 7/1996 | Fram et al. | |
| 5,571,147 A | 11/1996 | Sluijter et al. | |
| 5,588,964 A | 12/1996 | Imran et al. | |
| 5,599,295 A | 2/1997 | Rosen et al. | |
| 5,599,345 A | 2/1997 | Edwards et al. | |
| 5,626,576 A | 5/1997 | Janssen | |
| 5,672,174 A | 9/1997 | Gough et al. | |
| 5,683,382 A | 11/1997 | Lenihan et al. | |
| 5,688,266 A | 11/1997 | Edwards et al. | |
| 5,693,082 A | 12/1997 | Warner et al. | |
| 5,700,282 A | 12/1997 | Zabara | |
| 5,702,433 A | 12/1997 | Taylor et al. | |
| 5,707,400 A | 1/1998 | Terry, Jr. et al. | |
| 5,715,819 A | 2/1998 | Svenson et al. | |
| 5,741,249 A | 4/1998 | Moss et al. | |
| 5,772,590 A | 6/1998 | Webster, Jr. | |
| 5,775,338 A | 7/1998 | Hastings | |
| 5,782,760 A | 7/1998 | Schaer | |
| 5,800,494 A | 9/1998 | Campbell et al. | |
| 5,810,803 A | 9/1998 | Moss et al. | |
| 5,860,974 A | 1/1999 | Abele | |
| 5,861,021 A | 1/1999 | Thome et al. | |
| 5,865,787 A | 2/1999 | Shapland et al. | |
| 5,893,885 A | 4/1999 | Webster, Jr. | |
| 5,904,709 A | 5/1999 | Arndt et al. | |
| 5,931,860 A | 8/1999 | Reid et al. | |
| 5,944,710 A | 8/1999 | Dev et al. | |
| 5,954,719 A | 9/1999 | Chen et al. | |
| 5,967,976 A | 10/1999 | Larsen et al. | |
| 5,983,141 A | 11/1999 | Sluijter et al. | |
| 6,004,269 A | 12/1999 | Crowley et al. | |
| 6,009,351 A * | 12/1999 | Flachman | A61B 18/1815 607/101 |
| 6,009,877 A | 1/2000 | Edwards | |
| 6,024,740 A | 2/2000 | Lesh et al. | |
| 6,033,397 A | 3/2000 | Laufer et al. | |
| 6,036,687 A | 3/2000 | Laufer et al. | |
| 6,056,744 A | 5/2000 | Edwards | |
| 6,066,134 A | 5/2000 | Eggers et al. | |
| 6,081,749 A | 6/2000 | Ingle et al. | |
| 6,091,995 A | 7/2000 | Ingle et al. | |
| 6,097,985 A * | 8/2000 | Kasevich | A61B 18/18 607/100 |
| 6,099,524 A | 8/2000 | Lipson et al. | |
| 6,117,101 A | 9/2000 | Diederich et al. | |
| 6,135,999 A | 10/2000 | Fanton et al. | |
| 6,142,993 A | 11/2000 | Whayne et al. | |
| 6,149,620 A | 11/2000 | Baker et al. | |
| 6,161,048 A | 12/2000 | Sluijter et al. | |
| 6,181,970 B1 | 1/2001 | Kasevich | |
| 6,216,704 B1 | 4/2001 | Ingle et al. | |
| 6,219,577 B1 | 4/2001 | Brown, III et al. | |
| 6,224,592 B1 | 5/2001 | Eggers et al. | |
| 6,224,624 B1 | 5/2001 | Lasheras et al. | |
| 6,233,490 B1 * | 5/2001 | Kasevich | A61B 18/18 606/33 |
| 6,246,912 B1 | 6/2001 | Sluijter et al. | |
| 6,251,128 B1 | 6/2001 | Knopp et al. | |
| 6,273,886 B1 | 8/2001 | Edwards et al. | |
| 6,283,951 B1 | 9/2001 | Flaherty et al. | |
| 6,292,695 B1 | 9/2001 | Webster, Jr. et al. | |
| 6,314,325 B1 | 11/2001 | Fitz | |
| 6,322,558 B1 | 11/2001 | Taylor et al. | |
| 6,322,559 B1 | 11/2001 | Daulton et al. | |
| 6,405,732 B1 | 6/2002 | Edwards et al. | |
| 6,413,255 B1 | 7/2002 | Stern | |
| 6,427,089 B1 * | 7/2002 | Knowlton | A61B 18/18 607/101 |
| 6,471,696 B1 | 10/2002 | Berube et al. | |
| 6,477,426 B1 | 11/2002 | Fenn et al. | |
| 6,485,489 B2 | 11/2002 | Teirstein et al. | |
| 6,488,679 B1 | 12/2002 | Swanson et al. | |
| 6,490,488 B1 | 12/2002 | Rudie et al. | |
| 6,506,189 B1 | 1/2003 | Rittman, III et al. | |
| 6,514,226 B1 | 2/2003 | Levin et al. | |
| 6,522,926 B1 | 2/2003 | Kieval et al. | |
| 6,542,781 B1 | 4/2003 | Koblish et al. | |
| 6,551,310 B1 | 4/2003 | Ganz et al. | |
| 6,558,381 B2 | 5/2003 | Ingle et al. | |
| 6,562,034 B2 | 5/2003 | Edwards et al. | |
| 6,616,624 B1 | 9/2003 | Kieval | |
| 6,622,731 B2 | 9/2003 | Daniel et al. | |
| 6,635,054 B2 | 10/2003 | Fjield et al. | |
| 6,640,120 B1 | 10/2003 | Swanson et al. | |
| 6,652,515 B1 | 11/2003 | Maguire et al. | |
| 6,677,914 B2 | 1/2004 | Mertel | |
| 6,685,648 B2 | 2/2004 | Flaherty et al. | |
| 6,699,241 B2 | 3/2004 | Rappaport et al. | |
| 6,711,444 B2 | 3/2004 | Koblish | |
| 6,736,835 B2 | 5/2004 | Pellegrino et al. | |
| 6,740,108 B1 | 5/2004 | Just et al. | |
| 6,752,805 B2 | 6/2004 | Maguire et al. | |
| 6,788,977 B2 | 9/2004 | Fenn et al. | |
| 6,807,444 B2 | 10/2004 | Tu et al. | |
| 6,845,267 B2 | 1/2005 | Harrison et al. | |
| 6,847,848 B2 | 1/2005 | Sterzer et al. | |
| 6,850,801 B2 | 2/2005 | Kieval et al. | |
| 6,869,431 B2 | 3/2005 | Maguire et al. | |
| 6,885,888 B2 | 4/2005 | Rezai | |
| 6,893,436 B2 | 5/2005 | Woodard et al. | |
| 6,898,454 B2 | 5/2005 | Atalar et al. | |
| 6,917,834 B2 | 7/2005 | Koblish et al. | |
| 6,923,808 B2 | 8/2005 | Taimisto | |
| 6,932,776 B2 | 8/2005 | Carr | |
| 6,939,346 B2 | 9/2005 | Kannenberg et al. | |
| 6,949,097 B2 | 9/2005 | Stewart et al. | |
| 6,958,075 B2 | 10/2005 | Mon et al. | |
| 6,966,908 B2 | 11/2005 | Maguire et al. | |
| 6,974,456 B2 | 12/2005 | Edwards et al. | |
| 6,979,420 B2 | 12/2005 | Weber | |
| 7,097,641 B1 | 8/2006 | Arless et al. | |
| 7,149,574 B2 | 12/2006 | Yun et al. | |
| 7,162,303 B2 | 1/2007 | Levin et al. | |
| 7,192,427 B2 | 3/2007 | Chapelon et al. | |
| 7,221,979 B2 | 5/2007 | Zhou et al. | |
| 7,280,863 B2 | 10/2007 | Shachar | |
| 7,326,235 B2 | 2/2008 | Edwards | |

(56) References Cited

U.S. PATENT DOCUMENTS

| | | | |
|---|---|---|---|
| 7,381,200 B2 | 6/2008 | Katoh et al. | |
| 7,390,894 B2 | 6/2008 | Weinshilboum et al. | |
| 7,497,858 B2 | 3/2009 | Chapelon et al. | |
| 7,556,624 B2 | 7/2009 | Laufer et al. | |
| 7,617,005 B2 | 11/2009 | Demarais et al. | |
| 7,620,451 B2 | 11/2009 | Demarais et al. | |
| 7,647,115 B2 | 1/2010 | Levin et al. | |
| 7,653,438 B2 | 1/2010 | Deem et al. | |
| 7,717,948 B2 | 5/2010 | Demarais et al. | |
| 7,736,360 B2 | 6/2010 | Mody et al. | |
| 7,753,907 B2 | 7/2010 | DiMatteo et al. | |
| 7,778,703 B2 | 8/2010 | Gross et al. | |
| 7,811,313 B2 | 10/2010 | Mon et al. | |
| 7,833,220 B2 | 11/2010 | Mon et al. | |
| 7,837,720 B2 | 11/2010 | Mon | |
| 7,850,685 B2 | 12/2010 | Kunis et al. | |
| 7,869,854 B2 | 1/2011 | Shachar et al. | |
| 7,937,143 B2 | 5/2011 | Demarais et al. | |
| 8,131,371 B2 | 3/2012 | Demarals et al. | |
| 8,131,372 B2 * | 3/2012 | Levin | A61M 5/14276 607/44 |
| 8,140,170 B2 | 3/2012 | Rezai et al. | |
| 8,145,316 B2 | 3/2012 | Deem et al. | |
| 8,145,317 B2 | 3/2012 | Demarais et al. | |
| 8,150,518 B2 | 4/2012 | Levin et al. | |
| 8,150,519 B2 | 4/2012 | Demarais et al. | |
| 8,150,520 B2 | 4/2012 | Demarais et al. | |
| 8,175,711 B2 | 5/2012 | Demarais et al. | |
| 8,292,881 B2 | 10/2012 | Brannan et al. | |
| 8,308,722 B2 | 11/2012 | Ormsby et al. | |
| 8,343,145 B2 | 1/2013 | Brannan | |
| 8,401,667 B2 | 3/2013 | Gustus et al. | |
| 9,033,972 B2 * | 5/2015 | Curley | A61B 18/1815 606/33 |
| 9,089,542 B2 | 7/2015 | Azamian et al. | |
| 9,220,562 B2 | 12/2015 | Brannan et al. | |
| 9,333,035 B2 | 5/2016 | Rudie | |
| 9,358,066 B2 | 6/2016 | Brannan | |
| 9,387,038 B2 | 7/2016 | Brannan et al. | |
| 2001/0016762 A1 | 8/2001 | Carr | |
| 2002/0087151 A1 | 7/2002 | Mody et al. | |
| 2002/0115982 A1 | 8/2002 | Barbut et al. | |
| 2002/0139379 A1 | 10/2002 | Edwards et al. | |
| 2002/0143324 A1 | 10/2002 | Edwards | |
| 2002/0165532 A1 | 11/2002 | Hill et al. | |
| 2002/0183682 A1 | 12/2002 | Darvish et al. | |
| 2003/0050635 A1 | 3/2003 | Truckai et al. | |
| 2003/0050681 A1 | 3/2003 | Pianca et al. | |
| 2003/0060858 A1 | 3/2003 | Kieval et al. | |
| 2003/0065317 A1 | 4/2003 | Rudie et al. | |
| 2003/0069619 A1 | 4/2003 | Fenn et al. | |
| 2003/0074039 A1 | 4/2003 | Puskas | |
| 2003/0125790 A1 | 7/2003 | Fastovsky et al. | |
| 2003/0181897 A1 | 9/2003 | Thomas et al. | |
| 2003/0199863 A1 | 10/2003 | Swanson et al. | |
| 2003/0216792 A1 | 11/2003 | Levin et al. | |
| 2003/0220639 A1 | 11/2003 | Chapelon et al. | |
| 2003/0229340 A1 | 12/2003 | Sherry et al. | |
| 2003/0229384 A1 | 12/2003 | Mon | |
| 2003/0233099 A1 | 12/2003 | Danaek et al. | |
| 2004/0010289 A1 | 1/2004 | Biggs et al. | |
| 2004/0186468 A1 | 9/2004 | Edwards | |
| 2004/0215186 A1 | 10/2004 | Cornelius et al. | |
| 2004/0243199 A1 | 12/2004 | Mon et al. | |
| 2004/0254523 A1 | 12/2004 | Fitzgerald et al. | |
| 2005/0015081 A1 * | 1/2005 | Turovskiy | A61B 18/18 606/33 |
| 2005/0080409 A1 | 4/2005 | Young et al. | |
| 2005/0096647 A1 | 5/2005 | Steinke et al. | |
| 2005/0165389 A1 | 7/2005 | Swain et al. | |
| 2005/0165391 A1 | 7/2005 | Maguire et al. | |
| 2005/0187579 A1 | 8/2005 | Danek et al. | |
| 2005/0203498 A1 | 9/2005 | Mon et al. | |
| 2005/0228460 A1 | 10/2005 | Levin et al. | |
| 2005/0245920 A1 * | 11/2005 | Vitullo | A61B 18/18 606/33 |
| 2006/0085054 A1 | 4/2006 | Zikorus et al. | |
| 2006/0095029 A1 | 5/2006 | Young et al. | |
| 2006/0206150 A1 | 9/2006 | Demarais et al. | |
| 2006/0212076 A1 | 9/2006 | Demarais et al. | |
| 2006/0271111 A1 | 11/2006 | Demarais et al. | |
| 2007/0129720 A1 | 6/2007 | Demarais et al. | |
| 2007/0197891 A1 | 8/2007 | Shachar et al. | |
| 2007/0203480 A1 | 8/2007 | Mody et al. | |
| 2007/0265687 A1 | 11/2007 | Deem et al. | |
| 2007/0282407 A1 | 12/2007 | Demarais et al. | |
| 2008/0208169 A1 | 8/2008 | Boyle et al. | |
| 2008/0255642 A1 * | 10/2008 | Zarins | A61B 18/1206 607/99 |
| 2008/0319513 A1 | 12/2008 | Pu et al. | |
| 2009/0036948 A1 | 2/2009 | Levin et al. | |
| 2009/0076409 A1 | 3/2009 | Wu et al. | |
| 2010/0069818 A1 | 3/2010 | Smouse | |
| 2010/0076229 A1 | 3/2010 | Straub et al. | |
| 2010/0114086 A1 * | 5/2010 | Deem | A61B 18/18 606/33 |
| 2010/0125268 A1 | 5/2010 | Gustus et al. | |
| 2010/0137860 A1 | 6/2010 | Demarais et al. | |
| 2010/0137952 A1 | 6/2010 | Demarais et al. | |
| 2010/0174282 A1 | 7/2010 | Demarais et al. | |
| 2010/0191112 A1 | 7/2010 | Demarais et al. | |
| 2010/0191232 A1 | 7/2010 | Boveda | |
| 2010/0222851 A1 | 9/2010 | Deem et al. | |
| 2010/0222854 A1 | 9/2010 | Demarais et al. | |
| 2010/0298821 A1 | 11/2010 | Garbagnati | |
| 2011/0118720 A1 * | 5/2011 | Turner | A61B 18/1815 606/33 |
| 2011/0118723 A1 * | 5/2011 | Turner | A61B 18/1815 606/33 |
| 2011/0263921 A1 | 10/2011 | Vrba et al. | |
| 2011/0264086 A1 | 10/2011 | Ingle | |
| 2012/0029496 A1 * | 2/2012 | Smith | A61B 18/02 606/21 |
| 2012/0095461 A1 | 4/2012 | Herscher et al. | |
| 2012/0116486 A1 | 5/2012 | Naga et al. | |
| 2012/0130289 A1 | 5/2012 | Demarais et al. | |
| 2012/0130345 A1 | 5/2012 | Levin et al. | |
| 2012/0136350 A1 * | 5/2012 | Goshgarian | A61B 18/1492 606/41 |
| 2012/0143097 A1 | 6/2012 | Pike, Jr. | |
| 2012/0172837 A1 | 7/2012 | Demarais et al. | |
| 2012/0259326 A1 | 10/2012 | Brannan et al. | |
| 2013/0006232 A1 * | 1/2013 | Pellegrino | A61B 17/3472 606/33 |
| 2013/0012935 A1 * | 1/2013 | Pellegrino | A61B 17/3472 606/33 |
| 2013/0066316 A1 | 3/2013 | Steinke et al. | |
| 2013/0138095 A1 | 5/2013 | Gertner | |
| 2013/0274737 A1 | 10/2013 | Wang et al. | |
| 2014/0018888 A1 | 1/2014 | Ostroot et al. | |
| 2014/0031811 A1 | 1/2014 | Brannan | |
| 2014/0031812 A1 | 1/2014 | Brannan et al. | |
| 2014/0039487 A1 | 2/2014 | Brannan et al. | |
| 2014/0046313 A1 | 2/2014 | Pederson et al. | |
| 2014/0052125 A1 | 2/2014 | Bra et al. | |
| 2014/0257266 A1 | 9/2014 | Kasprzyk et al. | |
| 2014/0276743 A1 * | 9/2014 | Curley | A61B 18/1815 606/33 |
| 2015/0011989 A1 | 1/2015 | Azamian et al. | |
| 2015/0073211 A1 * | 3/2015 | Dickhans | A61B 1/0014 600/104 |
| 2015/0073407 A1 * | 3/2015 | Dickhans | A61B 18/1815 606/41 |
| 2015/0080875 A1 | 3/2015 | Kasprzyk et al. | |
| 2015/0119870 A1 * | 4/2015 | Rudie | A61B 18/1815 606/33 |
| 2016/0135885 A1 | 5/2016 | Brannan et al. | |
| 2016/0278859 A1 | 9/2016 | Brannan | |
| 2016/0302864 A1 | 10/2016 | Brannan et al. | |

(56) References Cited

U.S. PATENT DOCUMENTS

FOREIGN PATENT DOCUMENTS

| | | |
|---|---|---|
| EP | 1180004 | 2/2002 |
| EP | 2208506 | 7/2010 |
| EP | 2598071 | 6/2013 |
| EP | 2693969 A2 | 2/2014 |
| EP | 2693971 A2 | 2/2014 |
| EP | 2964127 A1 | 1/2016 |
| EP | 3001971 A1 | 4/2016 |
| EP | 3095407 A2 | 11/2016 |
| JP | 2003510126 | 3/2003 |
| WO | WO-199407446 | 4/1994 |
| WO | WO-9428809 | 12/1994 |
| WO | WO-1995025472 | 9/1995 |
| WO | WO-9531142 | 11/1995 |
| WO | WO-1997036548 | 10/1997 |
| WO | WO-9835638 | 8/1998 |
| WO | WO1998042403 | 10/1998 |
| WO | WO-9900060 | 1/1999 |
| WO | WO-9934741 | 7/1999 |
| WO | WO-0051513 | 9/2000 |
| WO | WO-0069376 | 11/2000 |
| WO | WO-2001022897 | 4/2001 |
| WO | WO-2001070114 | 9/2001 |
| WO | WO-0195820 | 12/2001 |
| WO | WO-02089686 | 11/2002 |
| WO | WO-02089871 | 11/2002 |
| WO | WO-03024309 | 3/2003 |
| WO | WO-2003022167 | 3/2003 |
| WO | WO-2003024309 | 3/2003 |
| WO | WO-2003082080 | 10/2003 |
| WO | WO-2004047659 | 6/2004 |
| WO | WO-2004064606 | 8/2004 |
| WO | WO-2004110258 | 12/2004 |
| WO | WO-2005007000 | 1/2005 |
| WO | WO-2005030072 | 4/2005 |
| WO | WO-2005041748 | 5/2005 |
| WO | WO-2005110528 | 11/2005 |
| WO | WO-2006041881 | 4/2006 |
| WO | WO-2006105121 | 10/2006 |
| WO | WO-2007008954 | 1/2007 |
| WO | WO-2007078997 | 7/2007 |
| WO | WO-2007113865 | 10/2007 |
| WO | WO-2008003058 | 1/2008 |
| WO | WO-2008049084 | 4/2008 |
| WO | WO-2010053700 | 5/2010 |
| WO | WO-2011055143 | 5/2011 |
| WO | WO-2012016137 | 2/2012 |
| WO | WO-2012061150 | 5/2012 |
| WO | WO-2012139135 | 10/2012 |
| WO | WO-2013106052 | 7/2013 |
| WO | WO-2013106053 | 7/2013 |
| WO | WO-2013106054 | 7/2013 |

OTHER PUBLICATIONS

Bello-Reuss, E. et al., "Effects of Acute Unilateral Renal Denervation in the Rat," Journal of Clinical Investigation, vol. 56, Jul. 1975, pp. 208-217.
Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.
Bhandari, A. and Ellias, M., "Loin Pain Hematuria Syndrome: Pain Control with RFA to the Splanchanic Plexus," The Pain Clinc, 2000, vol. 12, No. 4, pp. 323-327.
Curtis, John J. et al., "Surgical Therapy for Persistent Hypertension After Renal Transplantation" Transplantation, 31:125-128 (1981).
Dibona, Gerald F. et al., "Neural Control of Renal Function," Physiological Reviews, vol. 77, No. 1, Jan. 1997, The American Physiological Society 1997, pp. 75-197.
Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.

Janssen, Ben J.A. et al., "Effects of Complete Renal Denervation and Selective Afferent Renal Denervation on the Hypertension Induced by Intrarenal Norepinephrine Infusion in Conscious Rats", Journal of Hypertension 1989, 7: 447-455.
Katholi, Richard E., "Renal Nerves in the Pathogenesis of Hypertension in Experimental Animals and Humans," Am J. Physiol. vol. 245, 1983, The American Physiological Society 1983, pp. F1-F14.
Krum, Henry et al., "Catheter-Based Renal Sympathetic Denervation for Resistant Hypertension: A Mulitcentre Safety and Proof-of Principle Cohort Study," Lancet 2009; 373:1275-81.
Krum, et al., "Renal Sympathetic-Nerve Ablation for Uncontrolled Hypertension." New England Journal of Med, Aug. 2009, 361; 9, 3 pages.
Luippold, Gerd et al., "Chronic Renal Denervation Prevents Glomerular Hyperfiltration in Diabetic Rats", Nephrol Dial Transplant, vol. 19, No. 2, 2004, pp. 342-347.
Mahfoud et al. "Treatment strategies for resistant arterial hypertension" Dtsch Arztebl Int. 2011;108:725-731.
Osborn, et al., "Effect of Renal Nerve Stimulation on Renal Blood Flow Autoregulation and Antinatriuresis During Reductions in Renal Perfusion Pressure," Proceedings of the Society for Experimental Biology and Medicine, vol. 168, 77-81, 1981.
Page, I.H. et al., "The Effect of Renal Denervation on Patients Suffering From Nephritis," Feb. 27, 1935;443-458.
Page, I.H. et al., "The Effect of Renal Denervation on the Level of Arterial Blood Pressure and Renal Function in Essential Hypertension," J. Clin Invest. 1934;14:27-30.
Rocha-Singh, "Catheter-Based Sympathetic Renal Denervation," Endovascular Today, Aug. 2009, 4 pages.
Schlaich, M.P. et al., "Renal Denervation as a Therapeutic Approach for Hypertension: Novel Implications for an Old Concept," Hypertension, 2009; 54:1195-1201.
Schlaich, M.P. et al., "Renal Sympathetic-Nerve Ablation for Uncontrolled Hypertension," N Engl J Med 2009; 361(9): 932-934.
Smithwick, R.H. et al., "Splanchnicectomy for Essential Hypertension," Journal Am Med Assn, 1953; 152:1501-1504.
Symplicity HTN-1 Investigators; Krum H, Barman N, Schlaich M, et al. Catheter-based renal sympathetic denervation for resistant hypertension: durability of blood pressure reduction out to 24 months. Hypertension. 2011;57(5):911-917.
Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.
United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.
Valente, John F. et al., "Laparoscopic Renal Denervation for Intractable ADPKD-Related Pain", Nephrol Dial Transplant (2001) 16: 1 page.
Wagner, C.D. et al., "Very Low Frequency Oscillations in Arterial Blood Pressure After Autonomic Blockade in Conscious Dogs," Feb. 5, 1997, Am J Physiol Regul lntegr Comp Physiol 1997, vol. 272, 1997 the American Physiological Society, pp. 2034-2039.
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.
Avitall et al., "The creation of linear contiguous lesions in the atria with an expandable loop catheter,"Journal of the American College of Cardiology, 1999; 33; pp. 972-984.
Beale et al., "Minimally Invasive Treatment for Varicose Veins: A Review of Endovenous Laser Treatment and Radiofrequency Ablation". Lower Extremity Wounds 3(4), 2004, 10 pages.
Blessing, Erwin et al., Cardiac Ablation and Renal Denervation Systems Have Distinct Purposes and Different Technical Requirements, JACC Cardiovascular Interventions, vol. 6, No. 3, 2013, 1 page.
ClinicalTrials.gov, Renal Denervation in Patients with uncontrolled Hypertension in Chinese (2011), 6pages. www.clinicaltrials.gov/ct2/show/NCT01390831.

(56) References Cited

OTHER PUBLICATIONS

Excerpt of Operator's Manual of Boston Scientific's EPT-1000 XP Cardiac Ablation Controller & Accessories, Version of Apr. 2003, (6 pages).
Excerpt of Operator's Manual of Boston Scientific's Maestro 30000 Cardiac Ablation System, Version of Oct. 17, 2005, (4 pages).
Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.
Kandarpa, Krishna et al., "Handbook of Interventional Radiologic Procedures", Third Edition, pp. 194-210 (2002).
Mount Sinai School of Medicine clinical trial for Impact of Renal Sympathetic Denervation of Chronic Hypertension, Mar. 2013, 11 pages. http://clinicaltrials.gov/ct2/show/NCT01628198.
Opposition to European Patent No. EP1802370, Granted Jan. 5, 2011, Date of Opposition Oct. 5, 2011, 20 pages.
Opposition to European Patent No. EP2037840, Granted Dec. 7, 2011, Date of Opposition Sep. 7, 2012, 25 pages.
Opposition to European Patent No. EP2092957, Granted Jan. 5, 2011, Date of Opposition Oct. 5, 2011, 26 pages.
Oz, Mehmet, Pressure Relief, Time, Jan. 9, 2012, 2 pages. <www.time.come/time/printout/0,8816,2103278,00.html>.
Papademetriou, Vasilios, Renal Sympathetic Denervation for the Treatment of Difficult-to-Control or Resistant Hypertension, Int. Journal of Hypertension, 2011, 8 pages.
Pieper et al., "Design and Implementation of a New Computerized System for Intraoperative Cardiac Mapping." Journal of Applied Physiology, 1991, vol. 71, No. 4, pp. 1529-1539.
Prochnau, Dirk et al., Catheter-based renal denervation for drug-resistant hypertension by using a standard electrophysiology catheter; Euro Intervention 2012, vol. 7, pp. 1077-1080.
Purerfellner, Helmut et al., Incidence, Management, and Outcome in Significant Pulmonary Vein Stenosis Complicating Ablation for Atrial Fibrillation, Am. J. Cardiol, 93, Jun. 1, 2004, 4 pages.
Purerfellner, Helmut et al., Pulmonary Vein Stenosis Following Catheter Ablation of Atrial Fibrillation, Curr. Opin. Cardio. 20 :484-490, 2005.
Remo, Benjamin F. et al., "Safety and Efficacy of Renal Denervation as a Novel Treatment of Ventricular Tachycardia Storm in Patients with Cardiomyopathy." Heart Rhythm, 2014, 11(4), 541-6.
Schneider, Peter A., "Endovascular Skills—Guidewire and Catheter Skills for Endovascular Surgery," Second Edition Revised and Expanded, 10 pages, (2003).
ThermoCool Irrigated Catheter and Integrated Ablation System, Biosense Webster (2006), 6 pages.
Tsao, Hsuan-Ming, Evaluation of Pulmonary Vein Stenosis after Catheter Ablation of Atrial Fibrillation, Cardiac Electrophysiology Review, 6, 2002, 4 pages.
U.S. Appl. No. 60/852,787, filed Oct. 18, 2006, 112 pages.
Wittkampf et al., "Control of radiofrequency lesion size by power regulation," Journal of the American Heart Associate, 1989, 80: pp. 962-968.
Zheng et al., "Comparison of the temperature profile and pathological effect at unipolar, bipolar and phased radiofrequency current configurations," Journal of Interventional Cardiac Electrophysiology, 2001, pp. 401-410.
U.S. Appl. No. 95/002,110, filed Aug. 29, 2012, Demarais et al.
U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.
"2011 Edison Award Winners." Edison Awards: Honoring Innovations & Innovators, 2011, 6 pages, <http://www.edisonawards.com/BestNewProduct_2011.php>.
"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.
"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europer-innovation-award-and-demonstrates-further-durability-of-renal-denervation-treatment-for-hypertension-95545014.html>.
"Boston Scientific to Acquire Vessix Vascular, Inc.: Company to Strengthen Hypertension Program with Acquisition of Renal Denervation Technology." Boston Scientific: Advancing science for life-Investor Relations, Nov. 8, 2012, 2 pages, <http://phx.corporate-ir.net/phoenix.zhtml?c=62272&p=irol-newsArticle&id=1756108>.
"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.
"Does renal denervation represent a new treatment option for resistant hypertension?" Interventional News, Aug. 3, 2010, 2 pages. <http://www.cxvascular.com/in-latest-news/interventional-news---latest-news/does-renal-denervation-represent-a-new-treatment-option-for-resistant-hypertension>.
"Iberis—Renal Sympathetic Denervation System: Turning innovation into quality care." [Brochure], Terumo Europe N.V., 2013, Europe, 3 pages.
"Neurotech Reports Announces Winners of Gold Electrode Awards." Neurotech business report, 2009. 1 page. <http://www.neurotechreports.com/pages/goldelectrodes09.html>.
"Quick. Consistent. Controlled. OneShot renal Denervation System" [Brochure], Covidien: positive results for life, 2013, (n.l.), 4 pages.
"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.
"The Edison AwardsTM" Edison Awards: Honoring Innovations & Innovators, 2013, 2 pages, <http://www.edisonawards.com/Awards.php>.
"The Future of Renal denervation for the Treatment of Resistant Hypertension." St. Jude Medical, Inc., 2012, 12 pages.
"Vessix Renal Denervation System: So Advanced It's Simple." [Brochure], Boston Scientific: Advancing science for life, 2013, 6 pages.
Asbell, Penny, "Conductive Keratoplasty for the Correction of Hyperopia." Tr Am Ophth Soc, 2001, vol. 99, 10 pages.
Badoer, Emilio, "Cardiac afferents play the dominant role in renal nerve inhibition elicited by volume expansion in the rabbit." Am J Physiol Regul Integr Comp Physiol, vol. 274, 1998, 7 pages.
Bengel, Frank, "Serial Assessment of Sympathetic Reinnervation After Orthotopic Heart Transplantation: A longitudinal Study Using PET and C-11 Hydroxyephedrine." Circulation, vol. 99, 1999,7 pages.
Benito, F., et al. "Radiofrequency catheter ablation of accessory pathways in infants." Heart, 78:160-162 (1997).
Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.
Bohm, Michael et al., "Rationale and design of a large registry on renal denervation: the Global Symplicity registry." EuroIntervention, vol. 9, 2013, 9 pages.
Brosky, John, "EuroPCR 2013: CE-approved devices line up for renal denervation approval." Medical Device Daily, May 28, 2013,

(56) References Cited

OTHER PUBLICATIONS 3 pages, <http://www.medicaldevicedaily.com/servlet/com.accumedia.web.Dispatcher?next=bioWorldHeadlines_article&forceid=83002>.
Curtis, J.J., et al., "Surgical therapy for persistent hypertension after renal transplantation." Transplantation, 1981, 31: 125-128.
Davis, Mark et al., "Effectiveness of Renal Denervation Therapy for Resistant Hypertension." Journal of the American College of Cardiology, vol. 62, No. 3, 2013, 11 pp.
Dibona, G.F. "Sympathetic nervous system and kidney in hypertension." Nephrol and Hypertension, 11: 197-200 (2002).
Dibona, G.F., et al. "Neural control of renal function." Physiol Rev, 77:75-197 (1997).
Dubuc, M., et al., "Feasibility of cardiac cryoablation using a transvenous steerable electrode catheter." J Interv Cardiac Electrophysiol, 2:285-292 (1998).
Final Office Action; U.S. Appl. No. 12/827,700; dated Feb. 5, 2013, 61 pages.
Geisler, Benjamin et al., "Cost-Effectiveness and Clinical Effectiveness of Catheter-Based Renal Denervation for Resistant Hypertension." Journal of the American College of Cardiology, col. 60, No. 14, 2012, 7 pages.
Gelfand, M., et al., "Treatment of renal failure and hypertension." U.S. Appl. No. 60/442,970, filed Jan. 29, 2003, 23 pages.
Gertner, Jon, "Meet the Tech Duo That's Revitalizing The Medical Device Industry." FAST Company, Apr. 15, 2013, 6:00 AM, 17 pages, <http://www.fastcompany.com/3007845/meet-tech-duo-thats-revitalizing-medical-device-industry>.
Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).
Hall, W. H., et al. "Combined embolization and percutaneous radiofrequency ablation of a solid renal tumor." Am. J. Roentgenol,174: 1592-1594 (2000).
Han, Y.-M, et al., "Renal artery embolization with diluted hot contrast medium: An experimental study." J Vasc Interv Radiol, 12: 862-868 (2001).
Hansen, J.M., et al."The transplanted human kidney does not achieve functional reinnervation." Clin. Sci, 87: 13-19 (1994).
Hendee, W. R. et al. "Use of Animals in Biomedical Research: The Challenge and Response." American Medical Association White Paper (1988) 39 pages.
Hering, Dagmara et al., "Chronic kidney disease: role of sympathetic nervous system activation and potential benefits of renal denervation." EuroIntervention, vol. 9, 2013, 9 pages.
Huang et al., "Renal denervation prevents and reverses hyperinsulinemia-induced hypertension in rats." Hypertension 32 (1998) pp. 249-254.
Imimdtanz, "Medtronic awarded industry's highest honour for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.
Kaiser, Chris, AHA Lists Year's Big Advances in CV Research, medpage Today, Dec. 18, 2012, 4 pages, <http://www.medpagetoday.com/Cardiology/PCI/36509>.
Kompanowska, E., et al., "Early Effects of renal denervation in the anaesthetised rat: Natriuresis and increased cortical blood flow." J Physiol, 531. 2:527-534 (2001).
Lee, S.J., et al. "Ultrasonic energy in endoscopic surgery." Yonsei Med J, 40:545-549 (1999).
Linz, Dominik et al., "Renal denervation suppresses ventricular arrhythmias during acute ventricular ischemia in pigs." Heart Rhythm, vol. 0, No. 0, 2013, 6 pages.
Lustgarten, D.L.,et al., "Cryothermal ablation: Mechanism of tissue injury and current experience in the treatment of tachyarrhythmias." Progr Cardiovasc Dis, 41:481-498 (1999).
Mabin, Tom et al., "First experience with endovascular ultrasound renal denervation for the treatment of resistant hypertension." EuroIntervention, vol. 8, 2012, 5 pages.

Mahfoud, Felix et al., "Ambulatory Blood Pressure Changes after Renal Sympathetic Denervation in Patients with Resistant Hypertension." Circulation, 2013, 25 pages.
Mahfoud, Felix et al., "Expert consensus document from the European Society of Cardiology on catheter-based renal denervation." European Heart Journal, 2013, 9 pages.
Mahfoud, Felix et al., "Renal Hemodynamics and Renal Function After Catheter-Based Renal Sympathetic Denervation in Patients With Resistant Hypertension." Hypertension, 2012, 6 pages.
Medical-Dictionary.com, Definition of "Animal Model," http://medical-dictionary.com (search "Animal Model"), 2005, 1 page.
Medtronic, Inc., Annual Report (Form 10-K) (Jun. 28, 2011) 44 pages.
Millard, F. C., et al, "Renal Embolization for ablation of function in renal failure and hypertension." Postgraduate Medical Journal, 65, 729-734, (1989).
Oliveira, V., et al., "Renal denervation normalizes pressure and baroreceptor reflex in high renin hypertension in conscious rats." Hypertension, 19:II-17-II-21 (1992).
Ong, K. L., et al. "Prevalence, Awareness, Treatment, and Control of Hypertension Among United States Adults 1999-2004." Hypertension, 49: 69-75 (2007) (originally published online Dec. 11, 2006).
Ormiston, John et al., "First-in-human use of the OneShotTM renal denervation system from Covidien." EuroIntervention, vol. 8, 2013, 4 pages.
Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.
Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.
Peet, M., "Hypertension and its Surgical Treatment by bilateral supradiaphragmatic splanchnicectomy" Am J Surgery (1948) pp. 48-68.
Renal Denervation (RDN), Symplicity RDN System Common Q&A (2011), 4 pages, http://www.medtronic.com/rdn/mediakit/RDN%20FAQ.pdf.
Schauerte, P., et al."Catheter Ablation of Cardiac Autonomic Nerves for Prevention of Vagal Atrial Fibrillation." Circulation, 102:2774-2780 (2000).
Schlaich, Markus et al., "Renal Denervation in Human Hypertension: Mechanisms, Current Findings, and Future Prospects." Curr Hypertens Rep, vol. 14, 2012, 7 pages.
Schmid, Axel et al., "Does Renal Artery Supply Indicate Treatment Success of Renal Denervation." Cardiovasc Intervent Radiol, vol. 36, 2013, 5 pages.
Schmieder, Roland E. et al., "Updated ESH position paper on interventional therapy of resistant hypertension." EuroIntervention, vol. 9, 2013, 9 pages.
Sievert, Horst, "Novelty Award EuroPCR 2010." Euro PCR, 2010, 15 pages.
Smithwick et al., "Splanchnicectomy for essential hypertension." J. Am. Med. Assn. 152:16 (1953), pp. 1501-1504.
Solis-Herruzo et al., "Effects of lumbar sympathetic block on kidney function in cirrhotic patients with hepatorenal syndrome," J. Hepatol. 5 (1987), pp. 167-173.
Stella, A., et al., "Effects of reversable renal denervation on haemodynamic and excretory functions on the ipsilateral and contralateral kidney in the cat." Hypertension, 4: 181-188 (1986).
Stouffer, G. A. et al., "Catheter-based renal denervation in the treatment of resistant hypertension." Journal of Molecular and Cellular Cardiology, vol. 62, 2013, 6 pages.
Swartz, J.F., et al., "Radiofrequency endocardial catheter ablation of accessory atrioventricular pathway atrial insertion sites." Circulation, 87: 487-499 (1993).
Uchida, F., et al., "Effect of radiofrequency catheter ablation on parasympathetic denervation: A comparison of three different ablation sites." PACE, 21:2517-2521 (1998).
Valente, J.F. "Laparoscopic renal denervation for intractable ADPKD-related pain." Nephrol Dial Transplant, 16: 160 (2001).

(56) References Cited

OTHER PUBLICATIONS

Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.
Weinstock, M., et al., "Renal denervation prevents sodium retention and hypertension in salt sensitive rabbits with genetic baroreflex impairment." Clinical Science, 90:287-293 (1996).
Wilcox, Josiah N., Scientific Basis Behind Renal Denervation for the Control of Hypertension, ICI 2012, Dec. 5-6, 2012. 38 pages.
Worthley, Stephen et al., "Safety and efficacy of a multi-electrode renal sympathetic denervation system in resistant hypertension: the EnligHTN I trial." European Heart Journal, vol. 34, 2013, 9 pages.
Worthley, Stephen, "The St. Jude Renal Denervation System Technology and Clinical Review." The University of Adelaide Australia, 2012, 24 pages.
Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.
Miller, Reed, "Finding a Future for Renal Denervation With Better Controlled Trials." Pharma & Medtech Business Intelligence, Article # 01141006003, Oct. 6, 2014, 4 pages.
Papademetriou, Vasilios, "Renal Denervation and Symplicity HTN-3: "Dubium Sapientiae Initium" (Doubt Is the Beginning of Wisdom)", Circulation Research, 2014; 115: 211-214.
Papademetriou, Vasilios et al., "Renal Nerve Ablation for Resistant Hypertension: How Did We Get Here, Present Status, and Future Directions." Circulation. 2014; 129: 1440-1450.
Papademetriou, Vasilios et al., "Catheter-Based Renal Denervation for Resistant Hypertension: 12-Month Results of the EnligHTN I First-in-Human Study Using a Multielectrode Ablation System." Hypertension. 2014; 64: 565-572.
Doumas, Michael et al., "Renal Nerve Ablation for Resistant Hypertension: The Dust Has Not Yet Settled." The Journal of Clinical Hypertension. 2014; vol. 16, No. 6, 2 pages.
Messerli, Franz H. et al. "Renal Denervation for Resistant Hypertension: Dead or Alive?" Healio: Cardiology today's Intervention, May/Jun. 2014, 2 pages.
International Search Report and Written Opinion for International Application No. PCT/US2011/057729, dated Feb. 13, 2012, 13 pages.
Third-Party Submission Under 37 CFR 1.290 filed Dec. 12, 2012, 8 pp.
Third-Party Submission Under 37 CFR 1.290 filed Dec. 12, 2012, 22 pp.
Dodge, et al., "Lumen Diameter of Normal Human Coronary Arteries Influence of Age, Sex, Anatomic Variation, and Left Ventricular Hypertrophy or Dilation", Circulation, 1992, vol. 86 (1), 232-246 pp.
Opposition to European Patent No. 2465470, Granted Oct. 28, 2015, Date of Opposition Jul. 27, 2016, 34 pp.
U.S. Appl. No. 11/363,867, filed Feb. 27, 2006, 70 pp.
U.S. Appl. No. 60/813,589, filed Dec. 29, 2005, 62 pp.
Ureter, https://en.wikipedia.org/wiki/Ureter, Jun. 2016, 6 pp.

\* cited by examiner

*Arterial Vasculature*

*Venous Vasculature*

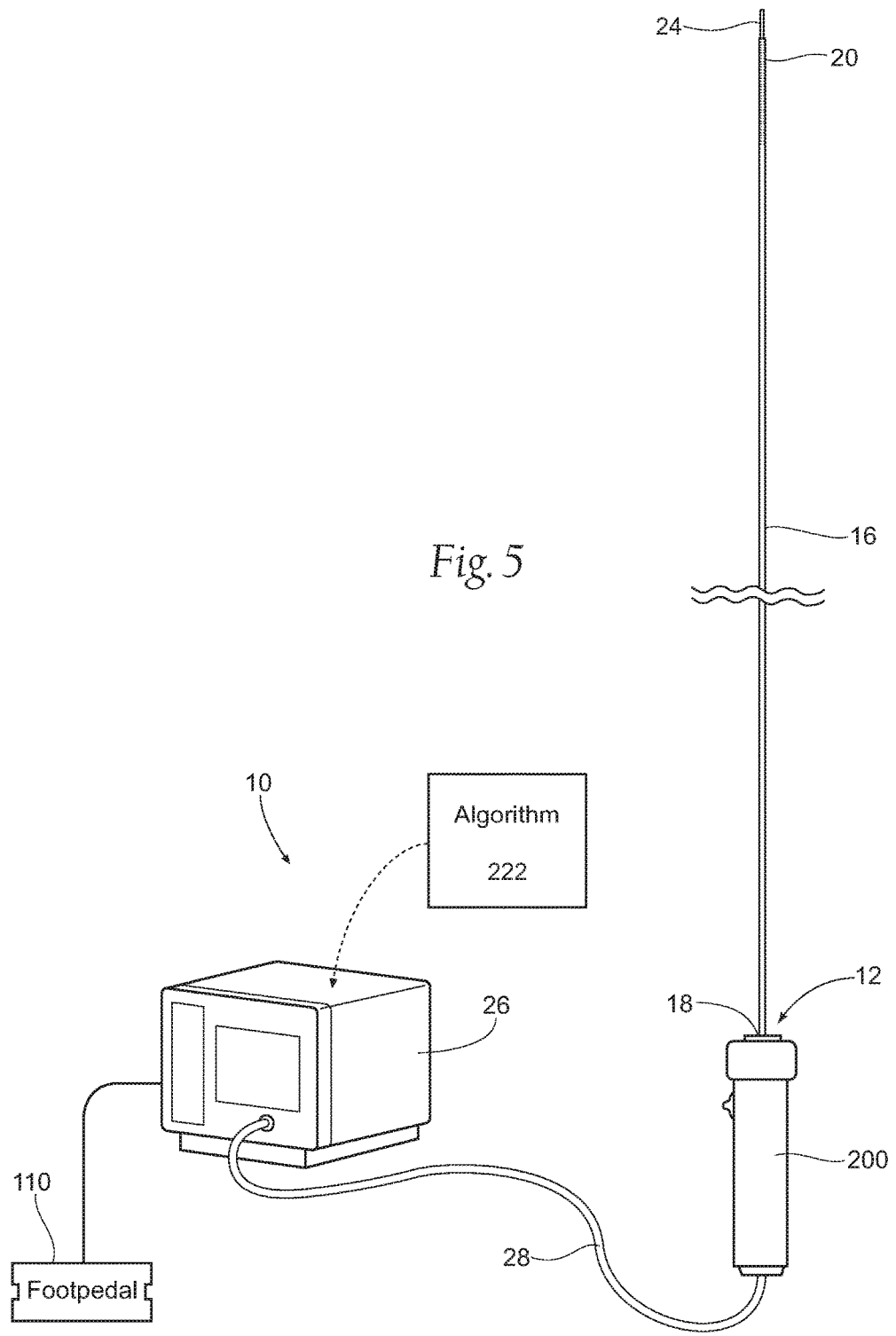

MICROWAVE CATHETER APPARATUSES, SYSTEMS, AND METHODS FOR RENAL NEUROMODULATION

CROSS-REFERENCE TO RELATED APPLICATION(S)

This application is a continuation of U.S. patent application Ser. No. 13/281,244, filed Oct. 25, 2011 which claims the benefit of U.S. Provisional Application No. 61/406,534, filed Oct. 25, 2010, and incorporated herein by reference in its entirety.

TECHNICAL FIELD

The technologies disclosed in the present application generally relate to catheter apparatuses, systems, and methods for intravascular neuromodulation. More particularly, the technologies disclosed herein relate to microwave catheter apparatuses, systems, and methods for achieving intravascular renal neuromodulation via dielectric heating.

BACKGROUND

The sympathetic nervous system (SNS) is a primarily involuntary bodily control system typically associated with stress responses. Fibers of the SNS innervate tissue in almost every organ system of the human body and can affect characteristics such as pupil diameter, gut motility, and urinary output. Such regulation can have adaptive utility in maintaining homeostasis or in preparing the body for rapid response to environmental factors. Chronic activation of the SNS, however, is a common maladaptive response that can drive the progression of many disease states. Excessive activation of the renal SNS in particular has been identified experimentally and in humans as a likely contributor to the complex pathophysiology of hypertension, states of volume overload (such as heart failure), and progressive renal disease. For example, radiotracer dilution has demonstrated increased renal norepinephrine (NE) spillover rates in patients with essential hypertension.

Cardio-renal sympathetic nerve hyperactivity can be particularly pronounced in patients with heart failure. For example, an exaggerated NE overflow from the heart and kidneys to plasma is often found in these patients. Heightened SNS activation commonly characterizes both chronic and end stage renal disease. In patients with end stage renal disease, NE plasma levels above the median have been demonstrated to be predictive for cardiovascular diseases and several causes of death. This is also true for patients suffering from diabetic or contrast nephropathy. Evidence suggests that sensory afferent signals originating from diseased kidneys are major contributors to initiating and sustaining elevated central sympathetic outflow.

Sympathetic nerves innervating the kidneys terminate in the blood vessels, the juxtaglomerular apparatus, and the renal tubules. Stimulation of the renal sympathetic nerves can cause increased renin release, increased sodium ($Na^+$) reabsorption, and a reduction of renal blood flow. These neural regulation components of renal function are considerably stimulated in disease states characterized by heightened sympathetic tone and likely contribute to increased blood pressure in hypertensive patients. The reduction of renal blood flow and glomerular filtration rate as a result of renal sympathetic efferent stimulation is likely a cornerstone of the loss of renal function in cardio-renal syndrome (i.e., renal dysfunction as a progressive complication of chronic heart failure). Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release), and diuretics (intended to counter the renal sympathetic mediated sodium and water retention). These pharmacologic strategies, however, have significant limitations including limited efficacy, compliance issues, side effects, and others. Accordingly, there is a strong public-health need for alternative treatment strategies.

BRIEF DESCRIPTION OF THE DRAWINGS

FIG. 5 is a perspective view of a microwave system for achieving intravascular renal neuromodulation, comprising a treatment device and a microwave generator.

DETAILED DESCRIPTION

Figure 1:
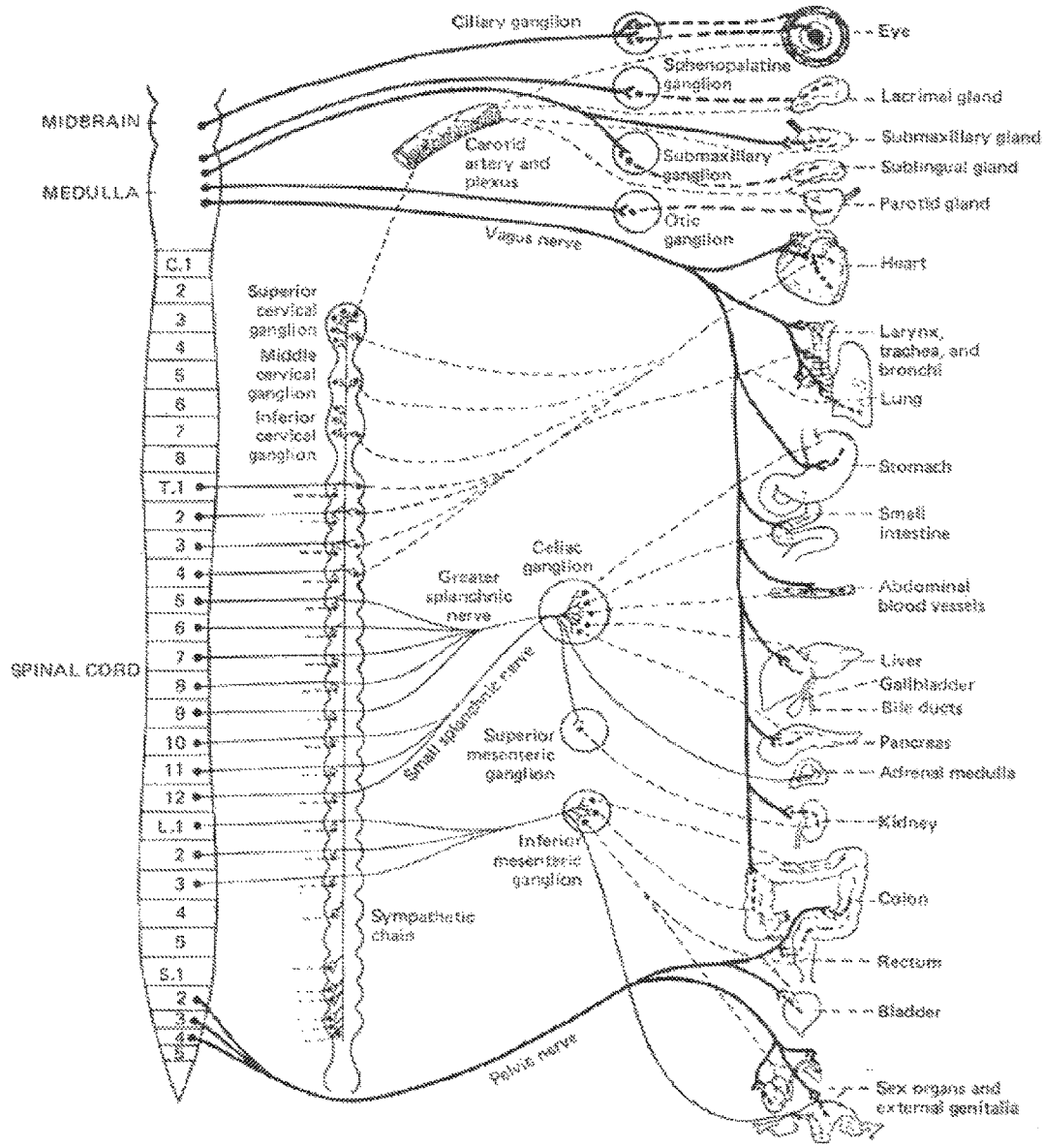
FIG. 1 is a conceptual illustration of the sympathetic nervous system (SNS) and how the brain communicates with the body via the SNS.

The present technology is directed to apparatuses, systems, and methods for achieving electrically- and/or thermally-induced renal neuromodulation (i.e., rendering neural fibers that innervate the kidney inert or inactive or otherwise completely or partially reduced in function) by percutaneous transluminal intravascular access. In particular, embodiments of the present technology relate to microwave apparatuses, systems, and methods that incorporate a catheter treatment device. The catheter treatment device may comprise an elongated shaft sized and configured to deliver at least one microwave transmission element within a renal artery via an intravascular path (e.g., a femoral artery, an iliac artery and the aorta, a transradial approach, or another suitable intravascular path). In one embodiment, for example, the microwave transmission element comprises an antenna that radiates microwaves within the renal artery in order to induce dielectric heating of target renal nerves or of vascular structures that perfuse target renal nerves. Microwaves are generated by a microwave generator, transferred along a feed or transmission line, and then radiated by the antenna. The microwave generator may be positioned along or near a proximal region of the elongated shaft external to the patient, while the feed line extends along or within the elongated shaft, and the antenna is positioned along a distal region of the shaft configured for placement in the renal artery via the intravascular path.

Specific details of several embodiments of the technology are described below with reference to FIGS. 1-23E. Although many of the embodiments are described below with respect to devices, systems, and methods for intravascular modulation of renal nerves using microwave apparatuses, other applications and other embodiments in addition to those described herein are within the scope of the technology. Additionally, several other embodiments of the technology can have different configurations, components, or procedures from those described herein. A person of ordinary skill in the art, therefore, will accordingly understand that the technology can have other embodiments with additional elements, or the technology can have other embodiments without several of the features shown and described below with reference to FIGS. 1-23E.

As used herein, the terms "distal" and "proximal" define a position or direction with respect to the treating clinician or the clinician's control device (e.g., a handle assembly). "Distal" or "distally" are a position distant from or in a direction away from the clinician or clinician's control device. "Proximal" and "proximally" are a position near or in a direction toward the clinician or the clinician's control device.

I. Pertinent Anatomy and Physiology

The following discussion provides various details regarding pertinent patient anatomy and physiology. This section is intended to provide additional context regarding the disclosed technology and the therapeutic benefits associated with renal denervation, and to supplement and expand upon the disclosure herein regarding the relevant anatomy and physiology. For example, as mentioned below, several properties of the renal vasculature may inform the design of treatment devices and associated methods for achieving renal neuromodulation via intravascular access, and impose specific design requirements for such devices. Specific design requirements may include accessing the renal artery, facilitating stable contact between the energy delivery elements of such devices and a luminal surface or wall of the renal artery, and/or effectively modulating the renal nerves with the neuromodulatory apparatus.

A. The Sympathetic Nervous System

The Sympathetic Nervous System (SNS) is a branch of the autonomic nervous system along with the enteric nervous system and parasympathetic nervous system. It is always active at a basal level (called sympathetic tone) and becomes more active during times of stress. Like other parts of the nervous system, the sympathetic nervous system operates through a series of interconnected neurons. Sympathetic neurons are frequently considered part of the peripheral nervous system (PNS), although many lie within the central nervous system (CNS). Sympathetic neurons of the spinal cord (which is part of the CNS) communicate with peripheral sympathetic neurons via a series of sympathetic ganglia. Within the ganglia, spinal cord sympathetic neurons join peripheral sympathetic neurons through synapses. Spinal cord sympathetic neurons are therefore called presynaptic (or preganglionic) neurons, while peripheral sympathetic neurons are called postsynaptic (or postganglionic) neurons.

At synapses within the sympathetic ganglia, preganglionic sympathetic neurons release acetylcholine, a chemical messenger that binds and activates nicotinic acetylcholine receptors on postganglionic neurons. In response to this stimulus, postganglionic neurons principally release noradrenaline (norepinephrine). Prolonged activation may elicit the release of adrenaline from the adrenal medulla.

Once released, norepinephrine and epinephrine bind adrenergic receptors on peripheral tissues. Binding to adrenergic receptors causes a neuronal and hormonal response. The physiologic manifestations include pupil dilation, increased heart rate, occasional vomiting, and increased blood pressure. Increased sweating is also seen due to binding of cholinergic receptors of the sweat glands.

The sympathetic nervous system is responsible for up- and down-regulating many homeostatic mechanisms in living organisms. Fibers from the SNS innervate tissues in almost every organ system, providing at least some regulatory function to things as diverse as pupil diameter, gut motility, and urinary output. This response is also known as sympatho-adrenal response of the body, as the preganglionic sympathetic fibers that end in the adrenal medulla (but also all other sympathetic fibers) secrete acetylcholine, which activates the secretion of adrenaline (epinephrine) and to a lesser extent noradrenaline (norepinephrine). Therefore, this response that acts primarily on the cardiovascular system is mediated directly via impulses transmitted through the sympathetic nervous system and indirectly via catecholamines secreted from the adrenal medulla.

Science typically looks at the SNS as an automatic regulation system, that is, one that operates without the intervention of conscious thought. Some evolutionary theorists suggest that the sympathetic nervous system operated in early organisms to maintain survival as the sympathetic nervous system is responsible for priming the body for action. One example of this priming is in the moments before waking, in which sympathetic outflow spontaneously increases in preparation for action.

1. The Sympathetic Chain

As shown in FIG. 1, the SNS provides a network of nerves that allows the brain to communicate with the body. Sympathetic nerves originate inside the vertebral column, toward the middle of the spinal cord in the intermediolateral cell column (or lateral horn), beginning at the first thoracic segment of the spinal cord and are thought to extend to the second or third lumbar segments. Because its cells begin in the thoracic and lumbar regions of the spinal cord, the SNS is said to have a thoracolumbar outflow. Axons of these nerves leave the spinal cord through the anterior rootlet/root. They pass near the spinal (sensory) ganglion, where they enter the anterior rami of the spinal nerves. However, unlike somatic innervation, they quickly separate out through white rami connectors which connect to either the paravertebral (which lie near the vertebral column) or prevertebral (which lie near the aortic bifurcation) ganglia extending alongside the spinal column.

In order to reach the target organs and glands, the axons should travel long distances in the body, and, to accomplish this, many axons relay their message to a second cell through synaptic transmission. The ends of the axons link across a space, the synapse, to the dendrites of the second cell. The first cell (the presynaptic cell) sends a neurotransmitter across the synaptic cleft where it activates the second cell (the postsynaptic cell). The message is then carried to the final destination.

In the SNS and other components of the peripheral nervous system, these synapses are made at sites called ganglia. The cell that sends its fiber is called a preganglionic cell, while the cell whose fiber leaves the ganglion is called a postganglionic cell. As mentioned previously, the preganglionic cells of the SNS are located between the first thoracic (T1) segment and third lumbar (L3) segments of the spinal cord. Postganglionic cells have their cell bodies in the ganglia and send their axons to target organs or glands.

The ganglia include not just the sympathetic trunks but also the cervical ganglia (superior, middle and inferior), which sends sympathetic nerve fibers to the head and thorax organs, and the celiac and mesenteric ganglia (which send sympathetic fibers to the gut).

2. Innervation of the Kidneys

Figure 2:
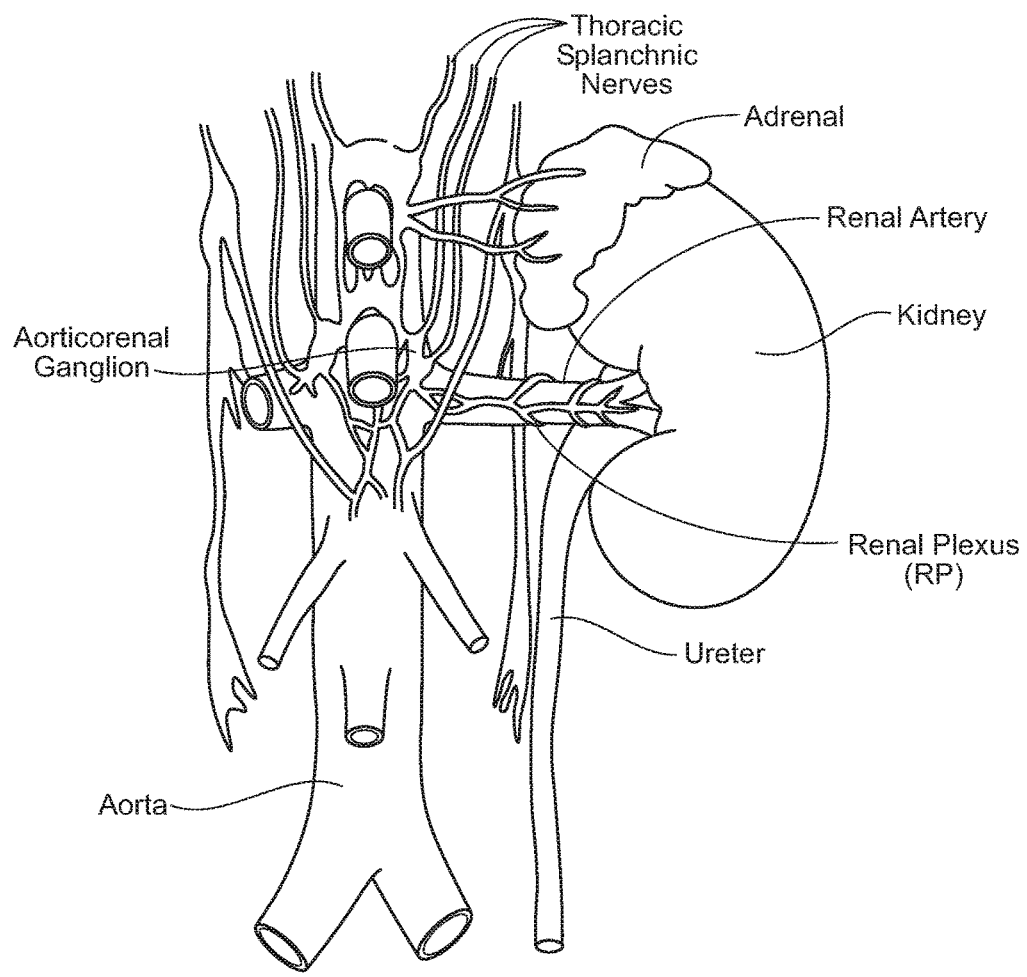
FIG. 2 is an enlarged anatomic view of nerves innervating a left kidney to form the renal plexus surrounding the left renal artery.

As FIG. 2 shows, the kidney is innervated by the renal plexus RP, which is intimately associated with the renal artery. The renal plexus RP is an autonomic plexus that surrounds the renal artery and is embedded within the adventitia of the renal artery. The renal plexus RP extends along the renal artery until it arrives at the substance of the kidney. Fibers contributing to the renal plexus RP arise from the celiac ganglion, the superior mesenteric ganglion, the aorticorenal ganglion and the aortic plexus. The renal plexus RP, also referred to as the renal nerve, is predominantly comprised of sympathetic components. There is no (or at least very minimal) parasympathetic innervation of the kidney.

Preganglionic neuronal cell bodies are located in the intermediolateral cell column of the spinal cord. Preganglionic axons pass through the paravertebral ganglia (they do not synapse) to become the lesser splanchnic nerve, the least splanchnic nerve, first lumbar splanchnic nerve, second lumbar splanchnic nerve, and travel to the celiac ganglion, the superior mesenteric ganglion, and the aorticorenal ganglion. Postganglionic neuronal cell bodies exit the celiac ganglion, the superior mesenteric ganglion, and the aorticorenal ganglion to the renal plexus RP and are distributed to the renal vasculature.

3. Renal Sympathetic Neural Activity

Messages travel through the SNS in a bidirectional flow. Efferent messages may trigger changes in different parts of the body simultaneously. For example, the sympathetic nervous system may accelerate heart rate; widen bronchial passages; decrease motility (movement) of the large intestine; constrict blood vessels; increase peristalsis in the esophagus; cause pupil dilation, piloerection (goose bumps) and perspiration (sweating); and raise blood pressure. Afferent messages carry signals from various organs and sensory receptors in the body to other organs and, particularly, the brain.

Hypertension, heart failure and chronic kidney disease are a few of many disease states that result from chronic activation of the SNS, especially the renal sympathetic nervous system. Chronic activation of the SNS is a maladaptive response that drives the progression of these disease states. Pharmaceutical management of the renin-angiotensin-aldosterone system (RAAS) has been a longstanding, but somewhat ineffective, approach for reducing over-activity of the SNS.

As mentioned above, the renal sympathetic nervous system has been identified as a major contributor to the complex pathophysiology of hypertension, states of volume overload (such as heart failure), and progressive renal disease, both experimentally and in humans. Studies employing radiotracer dilution methodology to measure overflow of norepinephrine from the kidneys to plasma revealed increased renal norepinephrine (NE) spillover rates in patients with essential hypertension, particularly so in young hypertensive subjects, which in concert with increased NE spillover from the heart, is consistent with the hemodynamic profile typically seen in early hypertension and characterized by an increased heart rate, cardiac output, and renovascular resistance. It is now known that essential hypertension is commonly neurogenic, often accompanied by pronounced sympathetic nervous system overactivity.

Activation of cardiorenal sympathetic nerve activity is even more pronounced in heart failure, as demonstrated by an exaggerated increase of NE overflow from the heart and the kidneys to plasma in this patient group. In line with this notion is the recent demonstration of a strong negative predictive value of renal sympathetic activation on all-cause mortality and heart transplantation in patients with congestive heart failure, which is independent of overall sympathetic activity, glomerular filtration rate, and left ventricular ejection fraction. These findings support the notion that treatment regimens that are designed to reduce renal sympathetic stimulation have the potential to improve survival in patients with heart failure.

Both chronic and end stage renal disease are characterized by heightened sympathetic nervous activation. In patients with end stage renal disease, plasma levels of norepinephrine above the median have been demonstrated to be predictive for both all-cause death and death from cardiovascular disease. This is also true for patients suffering from diabetic or contrast nephropathy. There is compelling evidence suggesting that sensory afferent signals originating from the diseased kidneys are major contributors to initiating and sustaining elevated central sympathetic outflow in this patient group; this facilitates the occurrence of the well known adverse consequences of chronic sympathetic over activity, such as hypertension, left ventricular hypertrophy, ventricular arrhythmias, sudden cardiac death, insulin resistance, diabetes, and metabolic syndrome.

(i) Renal Sympathetic Efferent Activity

Sympathetic nerves to the kidneys terminate in the blood vessels, the juxtaglomerular apparatus and the renal tubules. Stimulation of the renal sympathetic nerves causes increased renin release, increased sodium (Na+) reabsorption, and a reduction of renal blood flow. These components of the neural regulation of renal function are considerably stimulated in disease states characterized by heightened sympathetic tone and clearly contribute to the rise in blood pressure in hypertensive patients. The reduction of renal blood flow and glomerular filtration rate as a result of renal sympathetic efferent stimulation is likely a cornerstone of the loss of renal function in cardio-renal syndrome, which is renal dysfunction as a progressive complication of chronic heart failure, with a clinical course that typically fluctuates with the patient's clinical status and treatment. Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release) and diuretics (intended to counter the renal sympathetic mediated sodium and water retention). However, the current pharmacologic strategies have significant limitations including limited efficacy, compliance issues, side effects and others.

(ii) Renal Sensory Afferent Nerve Activity

Figure 3A:
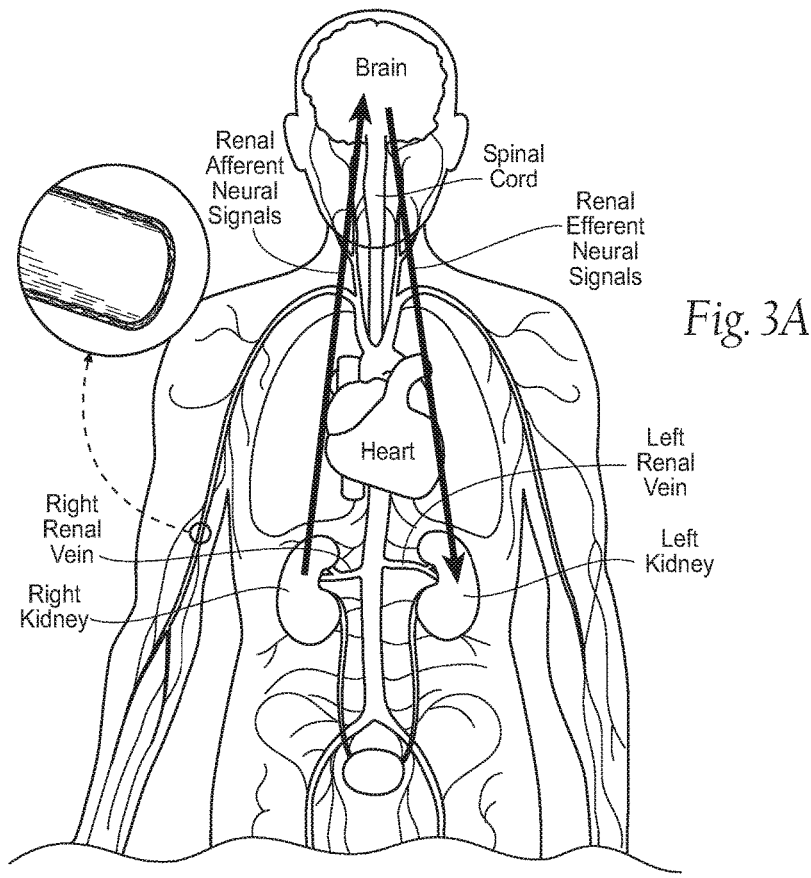
FIGS. 3A and 3B provide, respectively, anatomic and conceptual views of a human body, depicting neural efferent and afferent communication between the brain and kidneys.
Figure 3B:
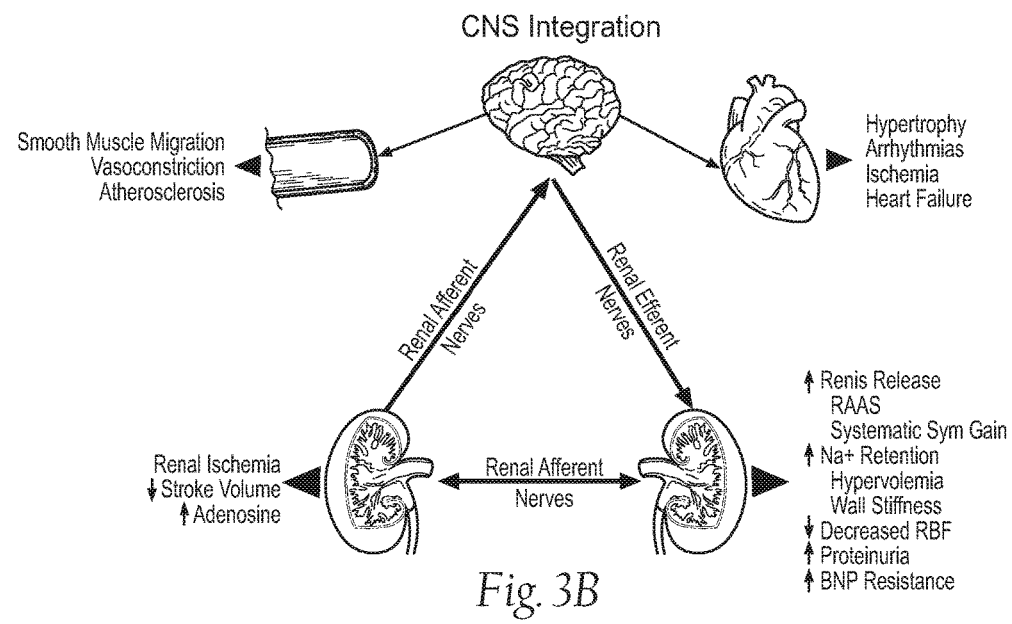

The kidneys communicate with integral structures in the central nervous system via renal sensory afferent nerves. Several forms of "renal injury" may induce activation of sensory afferent signals. For example, renal ischemia, reduction in stroke volume or renal blood flow, or an abundance of adenosine enzyme may trigger activation of afferent neural communication. As shown in FIGS. 3A and 3B, this afferent communication might be from the kidney to the brain or might be from one kidney to the other kidney (via the central nervous system). These afferent signals are centrally integrated and may result in increased sympathetic outflow. This sympathetic drive is directed towards the kidneys, thereby activating the RAAS and inducing increased renin secretion, sodium retention, volume retention and vasoconstriction. Central sympathetic over activity also impacts other organs and bodily structures innervated by sympathetic nerves such as the heart and the peripheral vasculature, resulting in the described adverse effects of sympathetic activation, several aspects of which also contribute to the rise in blood pressure.

The physiology therefore suggests that (i) modulation of tissue with efferent sympathetic nerves will reduce inappropriate renin release, salt retention, and reduction of renal blood flow, and that (ii) modulation of tissue with afferent sensory nerves will reduce the systemic contribution to hypertension and other disease states associated with increased central sympathetic tone through its direct effect on the posterior hypothalamus as well as the contralateral kidney. In addition to the central hypotensive effects of afferent renal denervation, a desirable reduction of central sympathetic outflow to various other sympathetically innervated organs such as the heart and the vasculature is anticipated.

B. Additional Clinical Benefits of Renal Denervation

As provided above, renal denervation is likely to be valuable in the treatment of several clinical conditions characterized by increased overall and particularly renal sympathetic activity such as hypertension, metabolic syndrome, insulin resistance, diabetes, left ventricular hypertrophy, chronic end stage renal disease, inappropriate fluid retention in heart failure, cardio-renal syndrome, and sudden death. Since the reduction of afferent neural signals contributes to the systemic reduction of sympathetic tone/drive, renal denervation might also be useful in treating other conditions associated with systemic sympathetic hyperactivity. Accordingly, renal denervation may also benefit other organs and bodily structures innervated by sympathetic nerves, including those identified in FIG. 1. For example, as previously discussed, a reduction in central sympathetic drive may reduce the insulin resistance that afflicts people with metabolic syndrome and Type II diabetics. Additionally, patients with osteoporosis are also sympathetically activated and might also benefit from the down regulation of sympathetic drive that accompanies renal denervation.

C. Achieving Intravascular Access to the Renal Artery

Figure 4A:
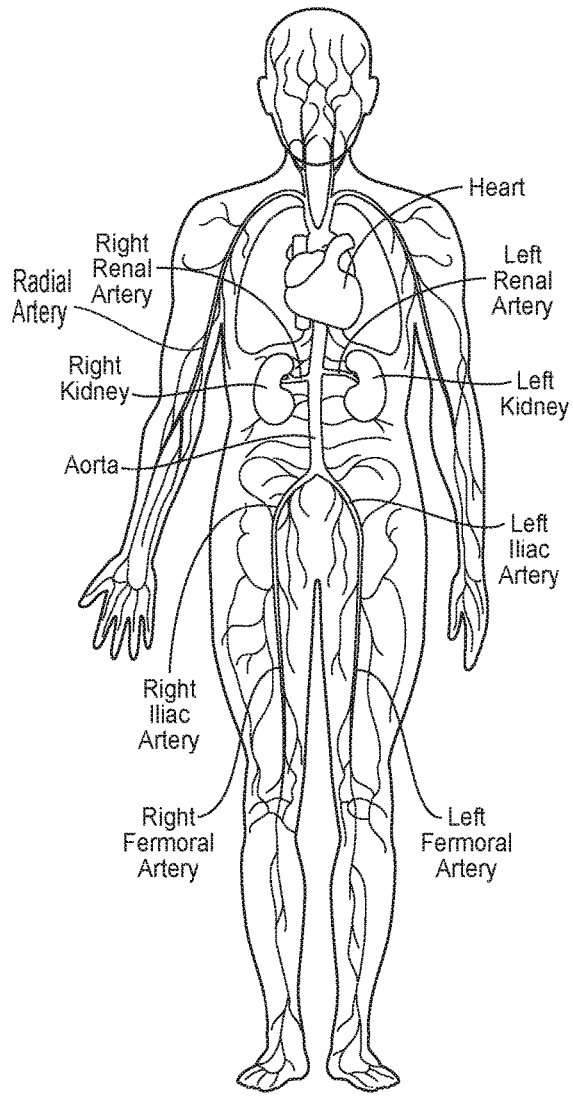
FIGS. 4A and 4B are, respectively, anatomic views of the arterial and venous vasculatures of a human.

In accordance with the present technology, neuromodulation of a left and/or right renal plexus RP, which is intimately associated with a left and/or right renal artery, may be achieved through intravascular access. As FIG. 4A shows, blood moved by contractions of the heart is conveyed from the left ventricle of the heart by the aorta. The aorta descends through the thorax and branches into the left and right renal arteries. Below the renal arteries, the aorta bifurcates at the left and right iliac arteries. The left and right iliac arteries descend, respectively, through the left and right legs and join the left and right femoral arteries.

Figure 4B:
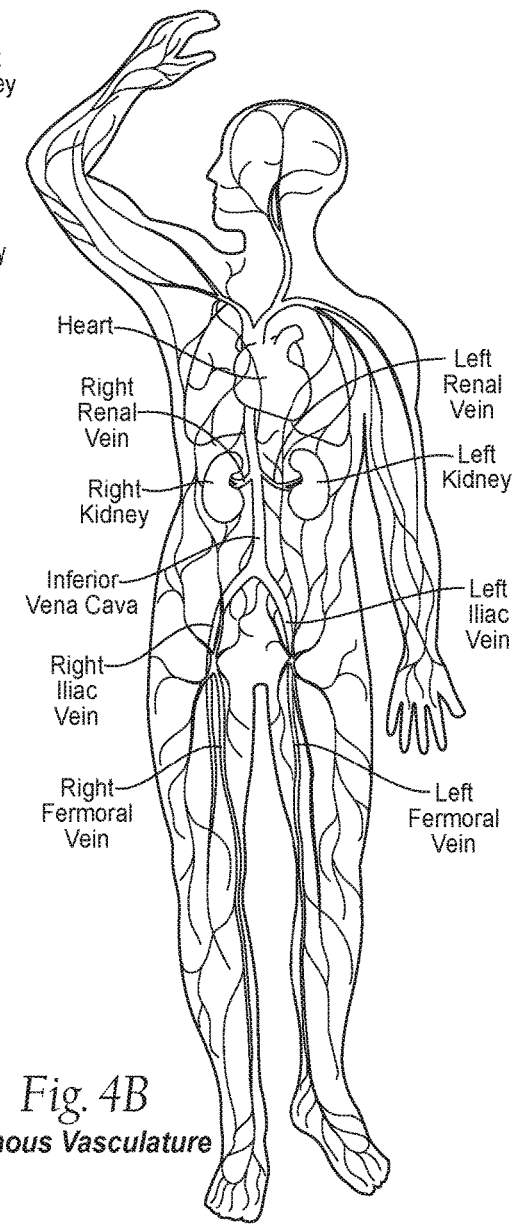

As FIG. 4B shows, the blood collects in veins and returns to the heart, through the femoral veins into the iliac veins and into the inferior vena cava. The inferior vena cava branches into the left and right renal veins. Above the renal veins, the inferior vena cava ascends to convey blood into the right atrium of the heart. From the right atrium, the blood is pumped through the right ventricle into the lungs, where it is oxygenated. From the lungs, the oxygenated blood is conveyed into the left atrium. From the left atrium, the oxygenated blood is conveyed by the left ventricle back to the aorta.

As will be described in greater detail later, the femoral artery may be accessed and cannulated at the base of the femoral triangle just inferior to the midpoint of the inguinal ligament. A catheter may be inserted percutaneously into the femoral artery through this access site, passed through the iliac artery and aorta, and placed into either the left or right renal artery. This comprises an intravascular path that offers minimally invasive access to a respective renal artery and/or other renal blood vessels.

The wrist, upper arm, and shoulder region provide other locations for introduction of catheters into the arterial system. For example, catheterization of either the radial, brachial, or axillary artery may be utilized in select cases. Catheters introduced via these access points may be passed through the subclavian artery on the left side (or via the subclavian and brachiocephalic arteries on the right side), through the aortic arch, down the descending aorta and into the renal arteries using standard angiographic technique.

D. Properties and Characteristics of the Renal Vasculature

Since neuromodulation of a left and/or right renal plexus RP may be achieved in accordance with the present technology through intravascular access, properties and characteristics of the renal vasculature may impose constraints upon and/or inform the design of apparatus, systems, and methods for achieving such renal neuromodulation. Some of these properties and characteristics may vary across the patient population and/or within a specific patient across time, as well as in response to disease states, such as hypertension, chronic kidney disease, vascular disease, end-stage renal disease, insulin resistance, diabetes, metabolic syndrome, etc. These properties and characteristics, as explained herein, may have bearing on the efficacy of the procedure and the specific design of the intravascular device. Properties of interest may include, for example, material/mechanical, spatial, fluid dynamic/hemodynamic and/or thermodynamic properties.

As discussed previously, a catheter may be advanced percutaneously into either the left or right renal artery via a minimally invasive intravascular path. However, minimally invasive renal arterial access may be challenging, for example, because as compared to some other arteries that are routinely accessed using catheters, the renal arteries are often extremely tortuous, may be of relatively small diameter, and/or may be of relatively short length. Furthermore, renal arterial atherosclerosis is common in many patients, particularly those with cardiovascular disease. Renal arterial anatomy also may vary significantly from patient to patient, which further complicates minimally invasive access. Significant inter-patient variation may be seen, for example, in relative tortuosity, diameter, length, and/or atherosclerotic plaque burden, as well as in the take-off angle at which a renal artery branches from the aorta. Apparatus, systems and methods for achieving renal neuromodulation via intravascular access should account for these and other aspects of renal arterial anatomy and its variation across the patient population when minimally invasively accessing a renal artery.

In addition to complicating renal arterial access, specifics of the renal anatomy also complicate establishment of stable contact between neuromodulatory apparatus and a luminal surface or wall of a renal artery. When the neuromodulatory apparatus includes an energy delivery element, such as an electrode, consistent positioning and appropriate contact force applied by the energy delivery element to the vessel wall are important for predictability. However, navigation is impeded by the tight space within a renal artery, as well as tortuosity of the artery. Furthermore, establishing consistent contact is complicated by patient movement, respiration, and/or the cardiac cycle because these factors may cause significant movement of the renal artery relative to the aorta, and the cardiac cycle may transiently distend the renal artery (i.e., cause the wall of the artery to pulse.

Even after accessing a renal artery and facilitating stable contact between neuromodulatory apparatus and a luminal surface of the artery, nerves in and around the adventia of the artery should be safely modulated via the neuromodulatory apparatus. Effectively applying thermal treatment from within a renal artery is non-trivial given the potential clinical complications associated with such treatment. For example, the intima and media of the renal artery are highly vulnerable to thermal injury. As discussed in greater detail below, the intima-media thickness separating the vessel lumen from its adventitia means that target renal nerves may be multiple millimeters distant from the luminal surface of the artery. Sufficient energy should be delivered to or heat removed from the target renal nerves to modulate the target renal nerves without excessively cooling or heating the vessel wall to the extent that the wall is frozen, desiccated, or otherwise potentially affected to an undesirable extent. A potential clinical complication associated with excessive heating is thrombus formation from coagulating blood flowing through the artery. Given that this thrombus may cause a kidney infarct, thereby causing irreversible damage to the kidney, thermal treatment from within the renal artery should be applied carefully. Accordingly, the complex fluid mechanics and thermodynamic conditions present in the renal artery during treatment, particularly those that may impact heat transfer dynamics at the treatment site, may be important in applying energy (e.g., heating thermal energy) and/or removing heat from the tissue (e.g., cooling thermal conditions) from within the renal artery.

The neuromodulatory apparatus should also be configured to allow for adjustable positioning and repositioning of the energy delivery element within the renal artery since location of treatment may also impact clinical efficacy. For example, it may be tempting to apply a full circumferential treatment from within the renal artery given that the renal nerves may be spaced circumferentially around a renal artery. In some situations, full-circle lesion likely resulting from a continuous circumferential treatment may be potentially related to renal artery stenosis. Therefore, the formation of more complex lesions along a longitudinal dimension of the renal artery via the mesh structures described herein and/or repositioning of the neuromodulatory apparatus to multiple treatment locations may be desirable. It should be noted, however, that a benefit of creating a circumferential ablation may outweigh the potential of renal artery stenosis or the risk may be mitigated with certain embodiments or in certain patients and creating a circumferential ablation could be a goal. Additionally, variable positioning and repositioning of the neuromodulatory apparatus may prove to be useful in circumstances where the renal artery is particularly tortuous or where there are proximal branch vessels off the renal artery main vessel, making treatment in certain locations challenging. Manipulation of a device in a renal artery should also consider mechanical injury imposed by the device on the renal artery. Motion of a device in an artery, for example by inserting, manipulating, negotiating bends and so forth, may contribute to dissection, perforation, denuding intima, or disrupting the interior elastic lamina.

Blood flow through a renal artery may be temporarily occluded for a short time with minimal or no complications. However, occlusion for a significant amount of time should be avoided because to prevent injury to the kidney such as ischemia. It could be beneficial to avoid occlusion all together or, if occlusion is beneficial to the embodiment, to limit the duration of occlusion, for example to 2-5 minutes.

Based on the above described challenges of (1) renal artery intervention, (2) consistent and stable placement of the treatment element against the vessel wall, (3) effective application of treatment across the vessel wall, (4) positioning and potentially repositioning the treatment apparatus to allow for multiple treatment locations, and (5) avoiding or limiting duration of blood flow occlusion, various independent and dependent properties of the renal vasculature that may be of interest include, for example, (a) vessel diameter, vessel length, intima-media thickness, coefficient of friction, and tortuosity; (b) distensibility, stiffness and modulus of elasticity of the vessel wall; (c) peak systolic, end-diastolic blood flow velocity, as well as the mean systolic-diastolic peak blood flow velocity, and mean/max volumetric blood flow rate; (d) specific heat capacity of blood and/or of the vessel wall, thermal conductivity of blood and/or of the vessel wall, and/or thermal convectivity of blood flow past a vessel wall treatment site and/or radiative heat transfer; (e) renal artery motion relative to the aorta induced by respiration, patient movement, and/or blood flow pulsatility: and (f) as well as the take-off angle of a renal artery relative to the aorta. These properties will be discussed in greater detail with respect to the renal arteries. However, dependent on the apparatus, systems and methods utilized to achieve renal neuromodulation, such properties of the renal arteries, also may guide and/or constrain design characteristics.

As noted above, an apparatus positioned within a renal artery should conform to the geometry of the artery. Renal artery vessel diameter, $D_{RA}$, typically is in a range of about 2-10 mm, with most of the patient population having a $D_{RA}$ of about 4 mm to about 8 mm and an average of about 6 mm. Renal artery vessel length, $L_{RA}$, between its ostium at the aorta/renal artery juncture and its distal branchings, generally is in a range of about 5-70 mm, and a significant portion of the patient population is in a range of about 20-50 mm. Since the target renal plexus is embedded within the adventitia of the renal artery, the composite Intima-Media Thickness, IMT, (i.e., the radial outward distance from the artery's luminal surface to the adventitia containing target neural structures) also is notable and generally is in a range of about 0.5-2.5 mm, with an average of about 1.5 mm. Although a certain depth of treatment is important to reach the target neural fibers, the treatment should not be too deep (e.g., >5 mm from inner wall of the renal artery) to avoid non-target tissue and anatomical structures such as the renal vein.

An additional property of the renal artery that may be of interest is the degree of renal motion relative to the aorta, induced by respiration and/or blood flow pulsatility. A patient's kidney, which located at the distal end of the renal artery, may move as much as 4" cranially with respiratory excursion. This may impart significant motion to the renal artery connecting the aorta and the kidney, thereby requiring from the neuromodulatory apparatus a unique balance of stiffness and flexibility to maintain contact between the thermal treatment element and the vessel wall during cycles of respiration. Furthermore, the take-off angle between the renal artery and the aorta may vary significantly between patients, and also may vary dynamically within a patient, e.g., due to kidney motion. The take-off angle generally may be in a range of about 30°-135°.

E. Achieving Renal Denervation via an Intravascularly Delivered Microwave Field

Microwave energy may be utilized to achieve renal neuromodulation via at least partial denervation of the kidney. For the purpose of this disclosure "microwave energy" and "microwave field" may be equivalent and interchangeable. Microwave energy is absorbed by tissue in a process called dielectric heating. Molecules in the tissue, such as water molecules, are electric dipoles that have a positive charge at one end and a negative charge at the other. The microwave energy induces an alternating electric field that causes the dipoles to rotate as they attempt to align themselves with the field. This molecular rotation generates heat as the molecules hit one another and cause additional motion. The heating is particularly efficient with liquid water molecules, which have a relatively high dipole moment. Tissue types that have relatively low water content, such as fat, do not absorb microwave energy as efficiently as other types of tissue.

The friction and heat produced through dipole rotation increases tissue temperature in a process known as dielectric heating, ultimately leading to cell death (i.e., necrosis) via coagulation. Accordingly, one feature of microwave-induced dielectric heating is that such an arrangement is expected to provide therapeutically high temperatures in target tissue, large and consistent ablation volumes, and/or relatively fast ablation times.

The renal arterial wall is comprised of intima, media and adventitia. Target renal nerves are positioned in and adjacent to the adventitia, and connective tissue surrounds the adventitia and nerves. Connective tissue is largely comprised of fat, which is a poor absorber of microwave energy due to its low water content, thereby reducing a risk of collateral damage to the fatty connective tissue during microwave irradiation of the renal nerves.

A microwave transmission element positioned within the renal artery via intravascular access may deliver a microwave field through the vessel wall and tissue, for example, omni-directionally in a plane relatively perpendicular to the longitudinal axis of the vessel. The microwave field may modulate (e.g., necrose), the target renal nerves. The depth to which the microwave field penetrates the wall and tissue is frequency dependent. Relatively greater microwave frequencies will provide relatively lower tissue penetration, while relatively lower microwave frequencies will provide relatively greater tissue penetration.

When delivered intravascularly, preferentially heating the adventitia while avoiding significant thermal exposure to the intima/media may be challenging. However, renal arterial blood flow may provide protective cooling of the intima/media. Alternatively, open or closed circuit cooling may be utilized to remove excess heat from the inner wall of the renal artery. Various methods, systems and apparatuses for active and open- and closed-circuit cooling have been described previously, for example, in U.S. patent application Ser. No. 13/279,205, filed Oct. 21, 2011, and International Patent App. No. PCT/US2011/033491, filed Apr. 21, 2011, both of which are incorporated herein by reference in their entireties.

II. Microwave Catheter Apparatuses, Systems, and Methods for Renal Neuromodulation A. Overview As just described, the left and/or right RP surrounds the respective left and/or right renal artery. The RP extends in intimate association with the respective renal artery into the substance of the kidney. FIG. 5 shows a microwave system 10 for inducing neuromodulation via dielectric heating of the left and/or right RP by intravascular access into the respective left or right renal artery.

The microwave system 10 includes an intravascular treatment device 12 such as a catheter with an elongated shaft 16 having a proximal end region 18 and a distal end region 20. The proximal end region 18 of the elongated shaft 16 is connected to a handle assembly 200. The distal end region 20 of the elongated shaft 16 carries at least one microwave transmission element 24, such as a microwave antenna 100 (see FIG. 7). The elongated shaft 16 is sized and configured for placement of its distal end region 20 within a renal artery by intravascular access. The microwave transmission element 24 is also specially sized and configured for manipulation and use within a renal artery.

The microwave system 10 also includes a microwave source or generator 26, such as a cavity magnetron, a klystron, a traveling wave tube, etc. Under the control of the caregiver or automated control algorithm 222, the microwave generator 26 generates a selected form and magnitude of microwave energy. The generator preferably generates microwaves at a medically acceptable frequency, such as 915 MHz, 2.45 GHz, and/or 5.1 GHz. As discussed previously, relatively greater microwave frequencies will provide relatively lower tissue penetration, while relatively lower microwave frequencies will provide relatively greater tissue penetration.

A feed or transmission line 28, such as a coaxial cable or a parallel wire, electrically transfers microwaves from the microwave generator 26 to the microwave transmission element 24 (e.g., extends along or within the elongated shaft 16 from the generator 26 to the transmission element 24). A control mechanism, such as foot pedal 110, can be connected (e.g., pneumatically or electrically) to the generator 26 to allow the operator to initiate, terminate and, optionally, adjust various operational characteristics of the microwave generator 26, including, but not limited to, microwave energy delivery. Optionally, one or more sensors, such as one or more temperature (e.g., thermocouple, thermistor, etc.), impedance, pressure, optical, flow, chemical or other sensors, can be located proximate to or within the microwave transmission element to monitor delivery of the microwave field and/or to monitor dielectric heating in the vicinity of the microwave transmission element (see FIG. 22B).

Figure 6A:
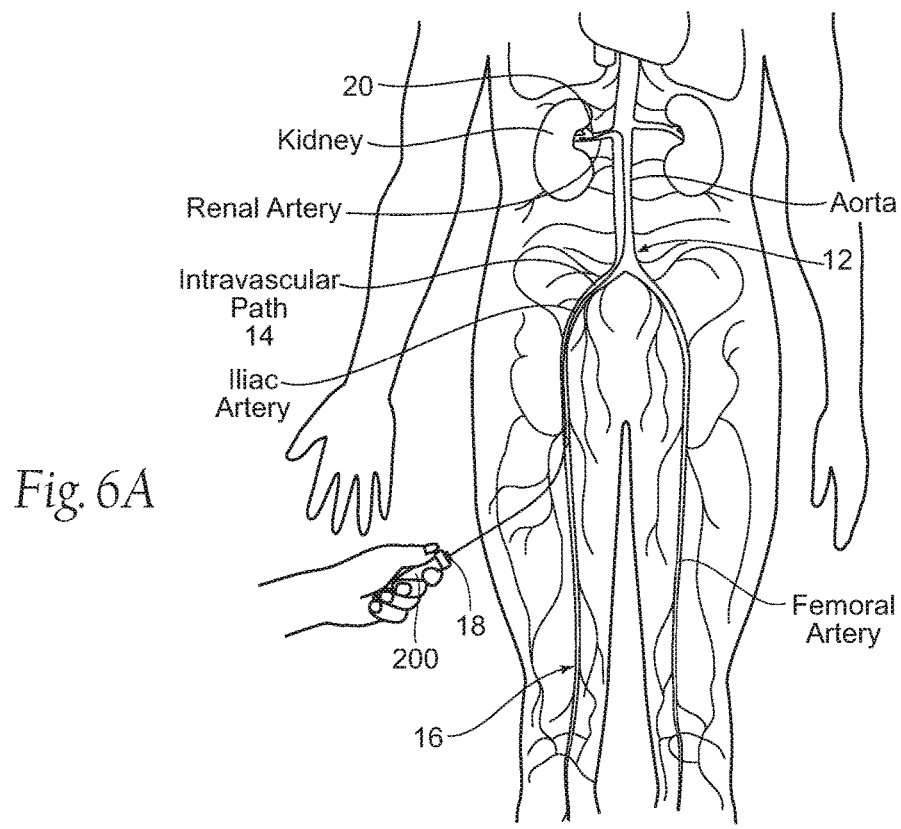
FIGS. 6A and 6B are, respectively, a schematic view illustrating placement of a distal region of the treatment device of FIG. 5 within a renal artery via an intravascular path, and a detailed schematic view of an embodiment of the distal region within the renal artery for delivery of microwave energy.

As shown in FIG. 6A, the treatment device 12 provides access to the RP through an intravascular path 14 that leads to a respective renal artery. The handle assembly 200 is sized and configured to be securely or ergonomically held and manipulated by a caregiver outside the intravascular path 14. By manipulating the handle assembly 200 from outside the intravascular path 14, the caregiver can advance the elongated shaft 16 through the sometimes tortuous intravascular path 14 and remotely manipulate or actuate the distal end region 20 if necessary. Image guidance (e.g., CT, radiographic, IVUS, OCT, or another suitable guidance modality, or combinations thereof), can be used to aid the caregiver's manipulation. Further, in some embodiments, image guidance components (e.g., IVUS, OCT) may be incorporated into the treatment device 12 itself.

Figure 6B:
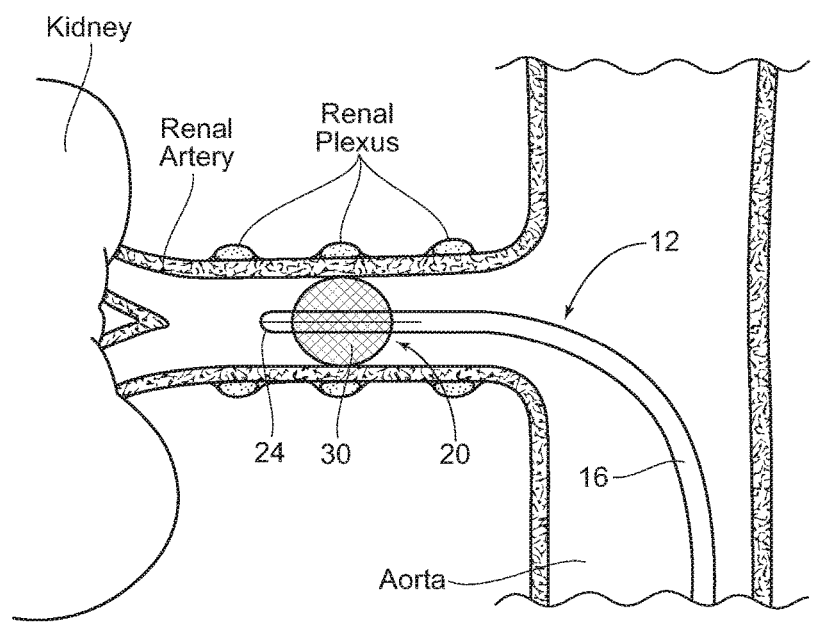
Figure 7:
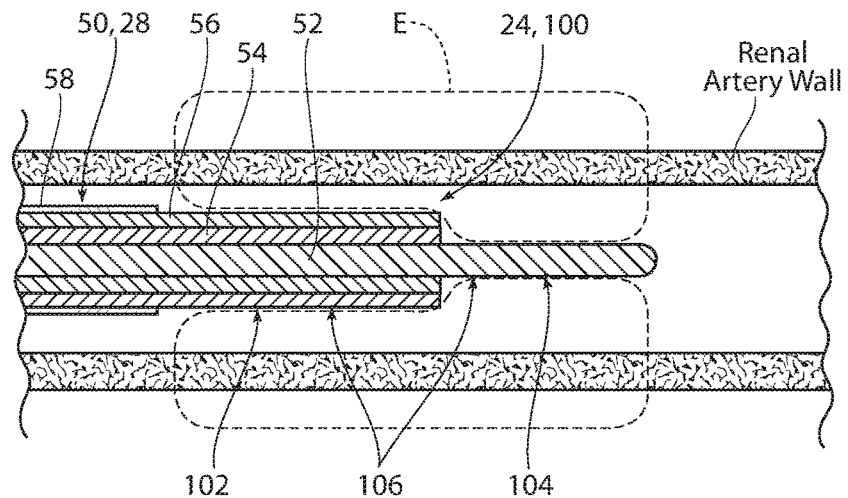
FIG. 7 is a schematic side-sectional view of the distal region of an embodiment of the microwave treatment device of FIG. 5 comprising a coaxial cable feed line and a coaxial antenna microwave transmission element.

As shown in FIG. 6B, the distal end region 20 of the elongated shaft 16 can flex in a substantial fashion to gain entrance into a respective left/right renal artery by manipulation of the elongated shaft 16. Optionally, the distal end region 20 of the elongated shaft 16 can gain entrance to the renal artery following a path defined by a guide catheter, a guide wire, or a sheath (not shown). In such cases, the maximum outer dimension (e.g., diameter) of any section of the elongated shaft 16, including the microwave transmission element 24 it carries, may be dictated by the inner diameter of the guide catheter through which the elongated shaft 16 is passed. Assuming, for example, that an 8 French guide catheter (which has an inner diameter of approximately 0.091 inch (2.31 mm)) would likely be, from a clinical perspective, the largest guide catheter used to access the renal artery, and allowing for a reasonable clearance tolerance between the elongated shaft 16 (i.e., microwave transmission element 24, centering element 30, etc.) and the guide catheter, the maximum outer dimension can realistically be expressed as being less than or equal to approximately 0.085 inch (2.16 mm). However, use of a smaller 5 French guide catheter may require the use of smaller outer diameters along the elongated shaft 16. For example, an elongated shaft 16 that is to be routed within a 5 French guide catheter may have an outer dimension of no greater than 0.053 inch (1.35 mm). In another example, an elongated shaft 16 that is to be routed within a 6 French guide catheter may have an outer dimension of no great than 0.070 inch (1.78 mm). In still further examples, other suitable guide catheters may be used, and outer dimensions and/or arrangements of the treatment device 12 can vary accordingly.

Once entrance to a renal artery is gained, the microwave transmission element 24 optionally may be aligned with tissue along an interior wall of the respective renal artery. Optionally, the microwave transmission element 24 also may be centered within the renal artery via, for example, an expandable centering element 30, such as a permeable centering element, an expandable braid or mesh, a cage, a basket, a balloon, stabilizing members, prongs, etc., that may be remotely expanded and collapsed via the handle assembly 200. The centering element 30 has a low-profile delivery configuration for intravascular delivery to, and retrieval from, within the renal artery (e.g., through a guide catheter), and an expanded deployed configuration (as seen in FIG. 6B) wherein the centering element 30 contacts the internal luminal surface of the renal artery and centers the microwave transmission element 24 within the artery.

Once the microwave transmission element 24 is positioned as desired within the renal artery, the purposeful application of microwave energy from the microwave generator 26 to tissue by radiation from the microwave transmission element 24 induces one or more desired neuromodulating effects on localized regions of the renal artery and adjacent regions of the RP, which lay intimately within or adjacent to the adventitia of the renal artery. The purposeful application of neuromodulating effects can achieve neuromodulation along all or a portion of the RP.

Neuromodulating effects can include thermal ablation, non-ablative thermal alteration, coagulation or damage (e.g., via sustained heating and/or dielectric heating), and electromagnetic neuromodulation. Desired dielectric heating effects may include raising the temperature of target neural fibers above a certain threshold to achieve non-ablative thermal alteration, or above a higher temperature to achieve ablative thermal alteration. For example, the target temperature can be above body temperature (e.g., approximately 37° C.) but less than about 45° C. for non-ablative thermal alteration, or the target temperature can be about 45° C. or higher for ablative thermal alteration. Desired non-thermal neuromodulation effects may include altering the electrical signals transmitted in a nerve.

Specific embodiments of the microwave system 10, along with associated methods and apparatuses, will now be described in further detail. These embodiments are provided merely for the sake of illustration and should in no way be construed as limiting.

B. Specific Embodiments

1. Coaxial Cable Feed Line and Coaxial Antenna Microwave Transmission Element

As discussed previously, microwaves are transferred from the microwave generator 26 to the microwave transmission element 24 via the feed line 28. As seen, for example, in FIG. 7, the feed line 28 may comprise a coaxial cable 50, and the microwave transmission element 24 may comprise, for example, a coaxial antenna 100. Coaxial cables and antennas are described, for example, in U.S. Pat. No. 2,184,729, to Bailey, which is incorporated herein by reference in its entirety. Microwave catheters for use in cardiac ablation procedures and comprising coaxial cables and antennas are described, for example, in U.S. Pat. No. 4,641,649 to Walinsky et al., which is incorporated herein by reference in its entirety.

Antennas convert electric current into electromagnetic radiation (and vice versa). The coaxial antenna 100 is a type of dipole antenna. The coaxial cable 50 connects the microwave generator 26 to the coaxial antenna 100. The coaxial cable 50 comprises an inner conductor 52, insulation 54 coaxially disposed about the inner conductor, and an outer conductor 56 comprising a tubular metal braid or shield that is coaxially disposed about the insulation 54. An outer delivery sheath or insulation 58 may cover the outer conductor 56. Microwave energy is delivered down the length of the coaxial cable 50 that terminates in the antenna 100 which is capable of radiating the energy into the surrounding tissue. The microwave energy is delivered through the space between the inner conductor 52 and the outer conductor 56. This space serves as a conduit while the outer conductor 56 prevents energy from escaping. Where a gap is encountered in the outer conductor 56 microwave energy is applied to the surrounding tissues. The gap may be perceived as an aperture instrumental in directing the microwave energy to the target in the controllable manner.

The insulation 54 between the inner and outer conductors 52, 56 electrically insulates and maintains a uniform distance between the inner conductor 52 and the outer conductor 56. The insulation 54 may comprise a dielectric material, such as solid or foamed PolyEthylene (PE) or PolyTetraFluoroEthylene (PTFE). The space between the inner and outer conductors 52, 56 may have an impedance that is approximately matched with the tissue impedance. An impedance mismatch between the antenna 100 and surrounding tissue may result in unbalanced currents on the inner and outer conductors 52, 56 of the feed line 28. In this case, a remainder current may flow along the outside of the outer conductor 56 of the feed line 28.

To form the coaxial antenna 100, an exposed element that is electrically connected to the inner conductor 52 is unshielded by the outer conductor 56. For example, the exposed element may be an extension of the inner conductor 52 or an electrically conductive element that is electrically connected to the inner conductor 52. The length of the exposed element may be a fraction of the wavelength of the microwave radiation (i.e., a fractional length), for example about ½ a wavelength. A distal region 102 of the outer conductor 56 of the coaxial cable 50 optionally is exposed (i.e., outer insulation or sheath 58 is optional) over a fractional length, for example, about ½ a wavelength. The distal regions 102 and 104 form a radiating element 106 of dipole coaxial antenna 100. When driven by a microwave signal generated by generator 26 and transferred by coaxial cable 50, the radiating element 106 of coaxial antenna 100 radiates microwaves outward in a torus or toroidal pattern. Microwave emission E is maximal and omni-directional in a plane perpendicular to the dipole (i.e., perpendicular to radiating element 106) and substantially reduced in the direction of the dipole.

2. Expandable Multi-Filament Centering Elements

It may be desirable to heat the renal nerves disposed within the adventitia while avoiding significant dielectric heating of the intima/media during microwave irradiation. Renal arterial blood flow may provide passive protective cooling of the intima/media. Thus, the centering element 30 may be permeable (such as in the expandable mesh/braid of FIG. 6B) and/or may not obstruct the entire vessel lumen, in order to ensure continued blood flow cooling of the renal artery intima/media during microwave-induced dielectric heating of target renal nerves. The centering element 30, and/or some other element, also may increase the velocity of blood flow at or near the vessel wall to enhance or accelerate the transfer of heat from the wall to the blood.

Figure 8A:
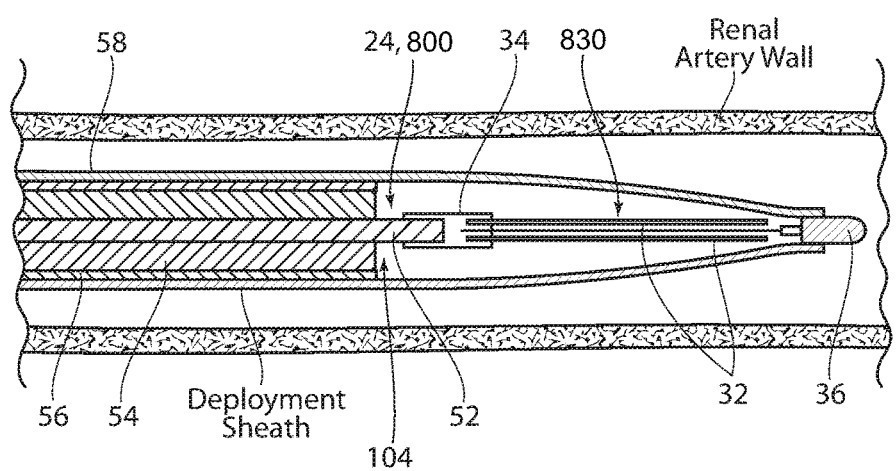
FIGS. 8A and 8B are schematic side-sectional views of the distal region of an embodiment of the microwave treatment device of FIG. 5 in a low-profile delivery configuration and in an expanded deployed configuration, including a multi-filament centering element.
Figure 8B:
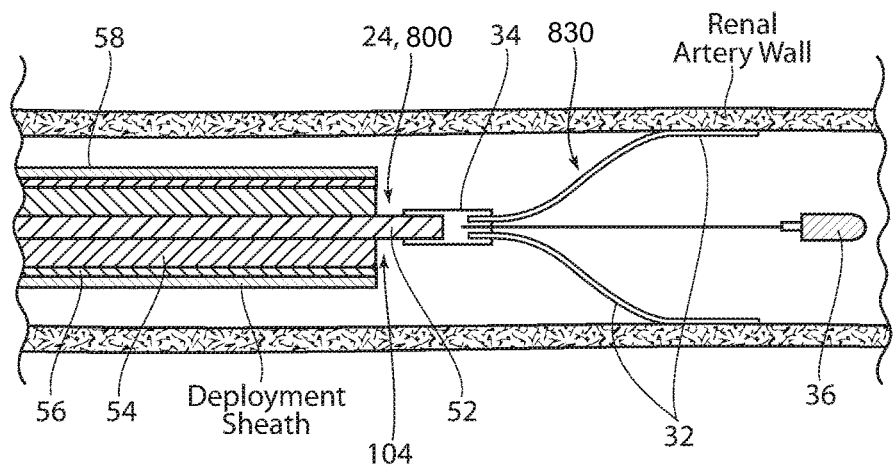

In FIGS. 8A and 8B, an expandable centering element 830 comprises a plurality of resilient filaments 32 (e.g., fingers or prongs), which are connected to the distal region 104 of inner conductor 52 at a connector 34. The connector 34 may be conductive or non-conductive, such that the centering element 830 may or may not, respectively, comprise a portion of the radiating element of an antenna 800. A nose cone 36 extends from connector 34, and all or a portion of the nose cone 36 also may or may not be conductive (i.e., may or may not comprise a portion of the radiating element), as desired. In embodiments in which expandable centering element 830 is not a portion of the radiating element, it may be made from a dielectric material such as a polymer or ceramic.

As seen in FIG. 8A, in the low-profile delivery configuration, the outer sheath 58 serves as a delivery sheath that extends and distally tapers to an attachment with the atraumatic nose cone 36, thereby constraining filaments 32. As seen in FIG. 8B, upon proximal retraction of the delivery sheath (e.g., via actuation of the handle assembly 200), the filaments 32 self-expand into contact with the vessel wall, thereby centering and aligning the coaxial antenna 800 with the longitudinal axis of the vessel.

Microwave radiation from the microwave generator 26 then may be transferred along the coaxial cable 50 to the antenna 800 and radiated omni-directionally into the vessel wall to target renal nerves. The microwaves dielectrically heat the target renal nerves, as discussed previously, which induces neuromodulation (e.g., denervation). Filaments 32 of the centering element 830 do not significantly obstruct blood flow, and thereby facilitate passive blood flow cooling of non-target intima and media. Upon completion of renal neuromodulation, microwave irradiation may be halted, and the centering element 830 may be collapsed for retrieval within the outer sheath 58 and/or within a guide catheter.

Figure 9:
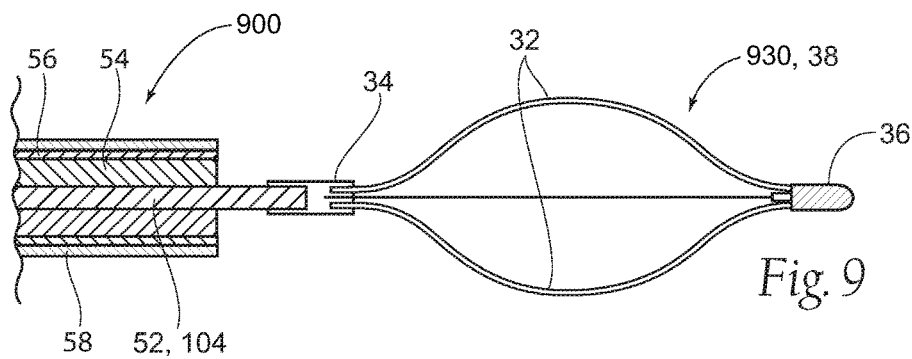
FIG. 9 is a schematic side-sectional view of the distal region of an alternative embodiment of the microwave treatment device of FIGS. 8A and 8B comprising an alternative multi-filament centering element.

With reference now to FIG. 9, an alternative embodiment of a centering element 930 is illustrated wherein filaments 32 are distally coupled to the nose cone 36 to form an expandable basket 38. The basket 38 may self-expand into contact with the vessel wall and/or may be actively expanded. FIG. 9 illustratively shows the basket 38 in the deployed configuration. Embodiments comprising expandable filaments or baskets for centering elements 930 may have a multiple number of filaments 32 (e.g., two, three, four, five, etc.), which may have variations of geometric shapes (e.g., straight, curved, helical, coiled, etc.).

3. Expandable Balloon Centering Elements

Figure 10A:
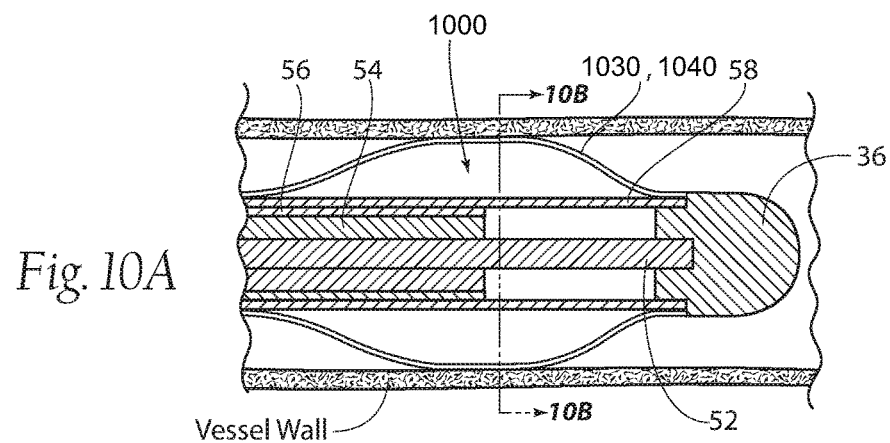
FIGS. 10A and 10B are, respectively, a schematic side-sectional view and a schematic cross-sectional view along section line 10B-10B of FIG. 10A of the distal region of an embodiment of the microwave treatment device of FIGS. 8A and 8B comprising an expandable balloon centering element.
Figure 10B:
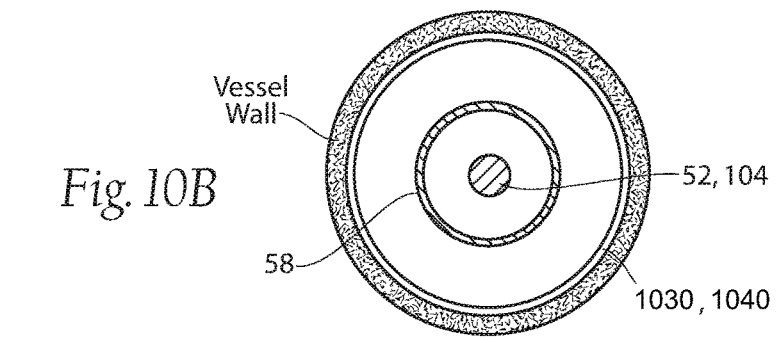

As seen in FIGS. 10A and 10B, an expandable centering element 1030 optionally may comprise an expandable balloon 1040. The balloon 1040 may be delivered in a low-profile configuration, expanded within the renal artery prior to and during application of the microwave field, and then collapsed for retrieval. As illustrated in the side-sectional view of FIG. 10A, expansion of the balloon 1040 into contact with the vessel wall may center an antenna 1000 within the vessel and align it with the longitudinal axis of the vessel to facilitate omni-directional microwave radiation into the wall. The balloon 1040 may be expanded by injecting a fluid/gas (e.g. nitrogen, carbon dioxide, saline, or other suitable liquids or gases) through an injection lumen (see, e.g., injection lumen 69 in FIG. 16). To contract the balloon the injected fluid or gas can be extracted through the same injection lumen, or through a separate lumen (not shown). A chilled fluid (e.g., chilled saline) may be used to inflate the balloon 1040 and may be circulated by injecting the fluid through an injection lumen and extracting the fluid through a separate extraction lumen to allow continuous or semi-continuous flow. Circulation of chilled fluid may have an added benefit of cooling the surface layers of the artery while allowing the deeper adventitia and renal nerves to heat and become neuromodulated (e.g., ablated).

As shown in FIG. 10A, a balloon may inflate to about the same diameter as the lumen of the artery and thereby occlude the artery (as shown in FIG. 10B). Alternatively (as illustrated in the cross-section of FIGS. 11A and 11B), the balloon 1040 may not completely obstruct the lumen of the renal artery, thereby allowing blood flow to cool and protect non-target intima and media during microwave irradiation of target renal nerves. By reducing the unobstructed cross-sectional area of the arterial lumen, the balloon 1040 may increase the velocity of blood flow through the unobstructed area, which may enhance the rate of heat transfer at the vessel wall along unobstructed portions of the lumen.

Figure 11A:
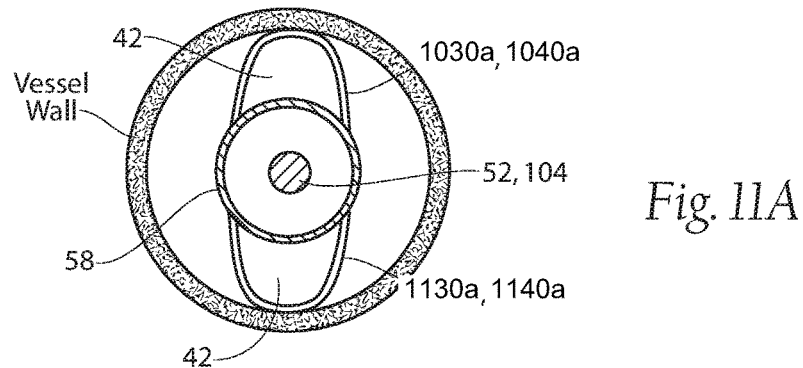
FIGS. 11A and 11B are schematic cross-sectional views of the distal region of alternative embodiments of the microwave treatment device of FIGS. 10A and 10B comprising an alternative expandable balloon centering element.
Figure 11B:
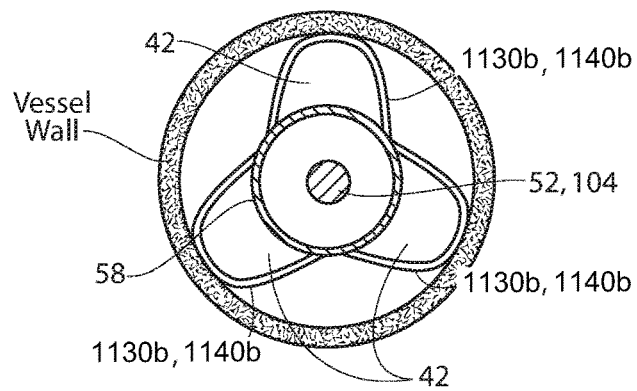

In FIG. 11A, a centering element 1130a comprises a balloon 1140a having two opposed lobes 42 that contact the inner wall of the renal artery. FIG. 11B illustrates an alternative embodiment of a centering element 1130b comprising a balloon 1140b having three lobes 42 spaced equidistantly about the circumference of the vessel. As will be apparent, balloons 1140a, 1140b may comprise any number of lobes, as desired.

Figure 12:
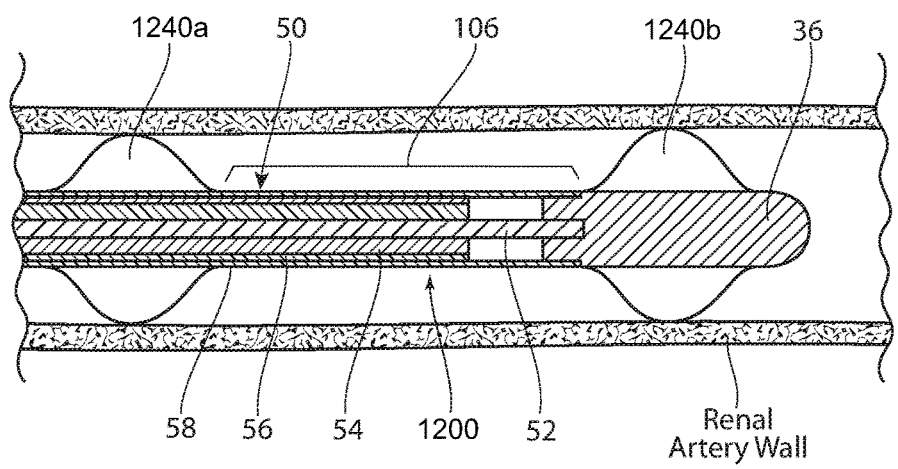
FIG. 12 is a schematic side-sectional view of the distal region of another alternative embodiment of the microwave treatment device of FIGS. 10A and 10B comprising another alternative expandable balloon centering element having proximal and distal balloons.

FIG. 12 illustrates another embodiment of an antenna 1200 having a plurality of balloons (illustrated individually as 1240a and 1240b) positioned proximal and distal of radiating section 106 of the antenna 1200. Optionally, the balloons 1240a and 1240b comprise multiple lobes and do not fully obstruct the lumen of the renal artery. Providing proximal and distal balloons may better center the antenna 1200 within the renal artery.

Figure 13:
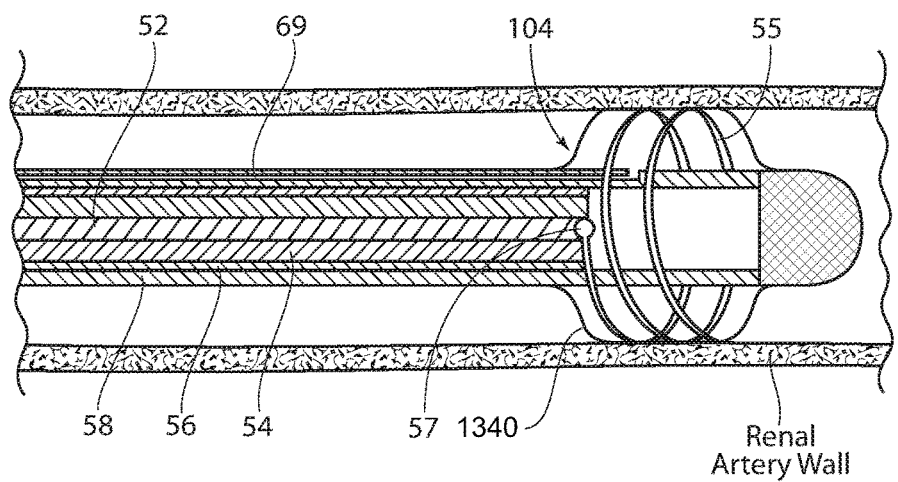
FIG. 13 is a schematic side-sectional view of the distal region of another alternative embodiment of the microwave treatment device of FIGS. 10A and 10B comprising another alternative expandable balloon centering element having conductive electrode traces applied on the surface of the balloon.

In another embodiment as shown in FIG. 13, an expandable balloon centering element 1340 and the distal region 104 of the inner conductor 52 may be combined such that the distal region 104 comprises one or more conductive electrode traces 55 applied on the surface of the balloon 1340 for improved microwave energy delivery. In this example, the emitting antenna is the metallic spiral pattern 55 applied or deposited on the inner or outer surface of the balloon 1340. Balloons comprising electrodes have been fabricated, for example, by MicroPen Technologies of Honeoye Falls, N.Y. The metallic spiral pattern 55 is electrically connected to the inner conductor 52 by a joint 57 that can be a weld or a solder joint. The antenna is thus implemented by a metalized path printed, deposited, or otherwise applied on the wall of the balloon 1340 and can be joined to the inner conductor 52 of the coaxial cable by an extension of the inner conductor 52 or by a separate interconnecting wire (not shown).

As in previous examples to form the antenna, the distal region 104 of the inner conductor 52 of the coaxial cable 50 is exposed over a length equal to a fraction of the wavelength of the microwave radiation. To achieve optimal length of the exposed inner conductor 52 and at the same time achieve the desired dimensions of the distal region 104 of the renal artery catheter, it may be desired to have the exposed conductor longer than the length of the balloon 1340. The proposed spiral pattern achieved when the balloon is expanded and the antenna is unfurled, is one of the many metallic surface patterns that can be used to achieve the desired length of the antenna in a compact device suitable for renal artery deployment. Alternative zigzag patterns can be proposed, for example, instead of a spiral. Common to these embodiments, the deposited metal forms an antenna that is electrically connected to one of the conductors in the feed line and is longer than the length of the balloon. The shape of the field expected from these embodiments is toroidal and substantially similar to the microwave field produced by the linear dipole antenna.

Figure 14:
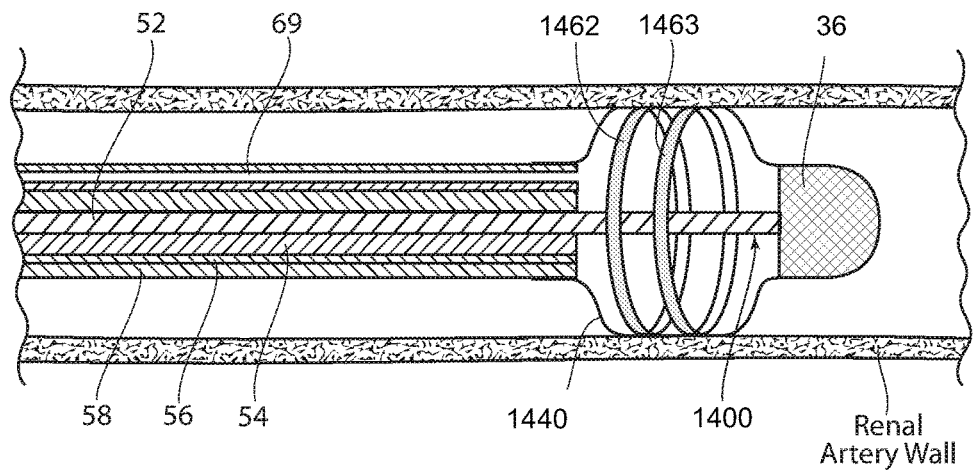
FIGS. 14 and 15 are schematic side-sectional views of the distal regions of other alternative embodiments of the microwave treatment device of FIGS. 10A and 10B comprising other alternative expandable balloon centering elements having one or more shields applied on the surface of the balloon.
Figure 15:
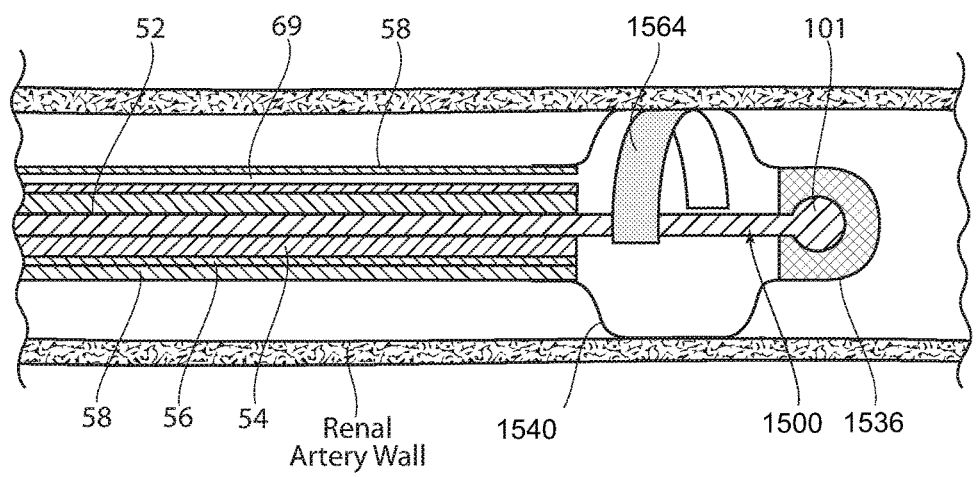

FIGS. 14 and 15 illustrate embodiments of antennas 1400 and 1500, respectively, where expandable balloon centering elements 1440 and 1540, respectively, comprise one or more conductive areas applied on the surfaces of the balloons for improved microwave energy delivery, where the conductive areas are not electrodes but shields.

The inner conductor 52 is in electric connection with the exposed segment of the antenna 1400, 1500 that is the emitter of the microwave field and energy. The applied metallic patterns 1462, 1463, and 1564 are not intended to emit energy but to reshape the microwave field and to improve the antennae matching network and thus ultimately change the geometry of the periarterial lesion. These designs can be useful when the toroidal shape of the microwave field is not desired in order to preferentially treat one area of the renal artery and spare another to reduce the risk of stenosis or for other medical reasons. In other words, to prevent direct penetration of microwaves into the tissue surrounding the balloon catheter, the balloon envelope is provided with a metallic coating in selected areas. The metallic patterns 1462, 1463, and 1564 and other possible patterns (e.g., helical shielding patterns or shielding lines that are parallel to the axis of the vessel) distort the microwave field and shield certain areas of the renal artery in a predictable fashion. The unprotected areas receive a relatively high concentration of microwave energy.

FIG. 15 also illustrates incorporation of a conductive element 101 into an atraumatic tip 1536. Such an element can be instrumental in tuning up the antenna. The nose cone 1536 can incorporate a cap useful in the cap and choke antennae designs intended to improve impedance matching. The choke is a conductive sleeve placed above the coaxial feed assembly right before the area where the emitter antenna emerges from the coaxial shield.

Figure 16:
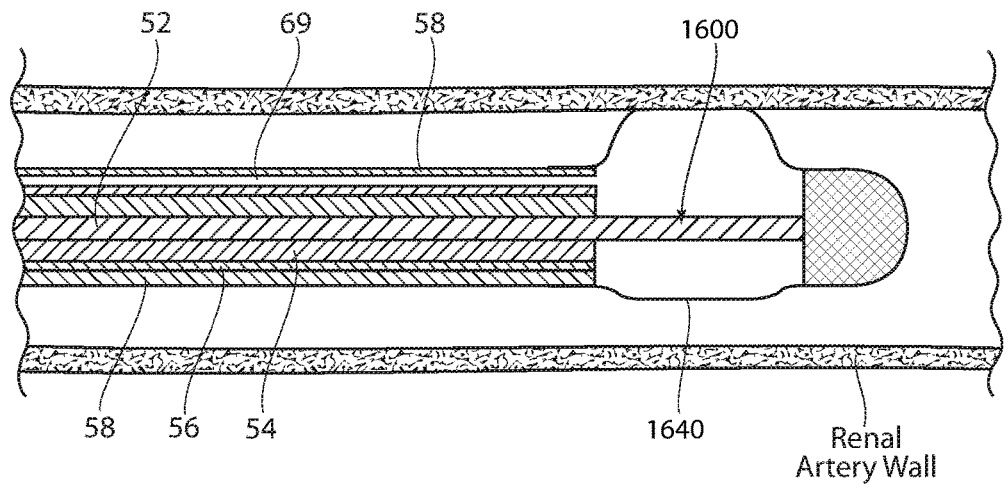
FIG. 16 is a schematic side-sectional view of the distal region of another alternative embodiment of the microwave treatment device of FIGS. 10A and 10B comprising another alternative expandable balloon that places the microwave antenna off-center within a vessel.

FIG. 16 illustrates an embodiment of an antenna 1600 where a balloon 1640 is asymmetric relative to the catheter shaft and the antenna 1600. The purpose of such a balloon 1640 is to increase the delivery of microwave energy to one side of the internal lumen of the renal artery and decrease the delivery to the opposite side.

4. Flow Directing Elements

Figure 17:
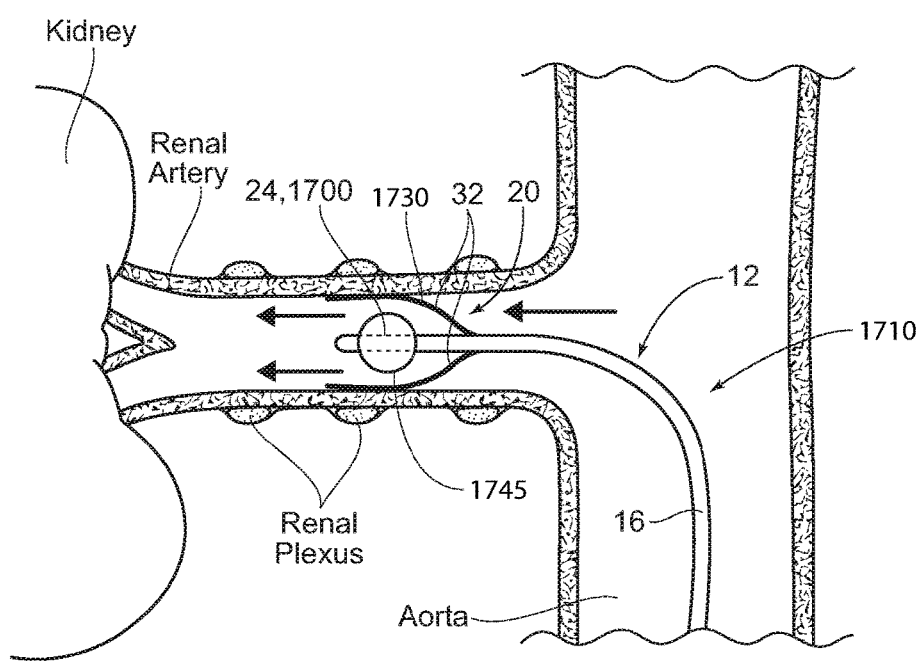
FIG. 17 is a schematic view of the distal region of an embodiment of the microwave treatment device of FIG. 5 comprising a flow directing element.

FIG. 17 illustrates an embodiment of a microwave system 1710 comprising an expandable centering element 1730 in combination with a flow directing velocity enhancement element 1745. In FIG. 17, the centering element 1730 illustratively comprises multiple resilient filaments 32, as discussed previously. Flow directing element 1745 illustratively comprises an expandable balloon having a diameter less than the diameter of the lumen of the renal artery in which treatment is conducted. Microwave transmitting element 24/antenna 1700 may be positioned within the flow directing element 1745.

In the expanded deployed configuration of FIG. 17, the centering element 1730 aligns and centers the antenna 1700 within the renal artery, while the flow directing element 1745 obstructs the center of the artery. This central obstruction directs blood flow around the flow directing element 1745 and toward the luminal wall of the renal artery, where protective cooling is desired during microwave irradiation and dielectric heating of the target renal nerves. The central obstruction also increases flow velocity, which in turn increases the rate of protective heat transfer from the vessel wall to the blood during such microwave irradiation.

5. Over-the-Wire and Rapid Exchange Microwave Catheters

Figure 18A:
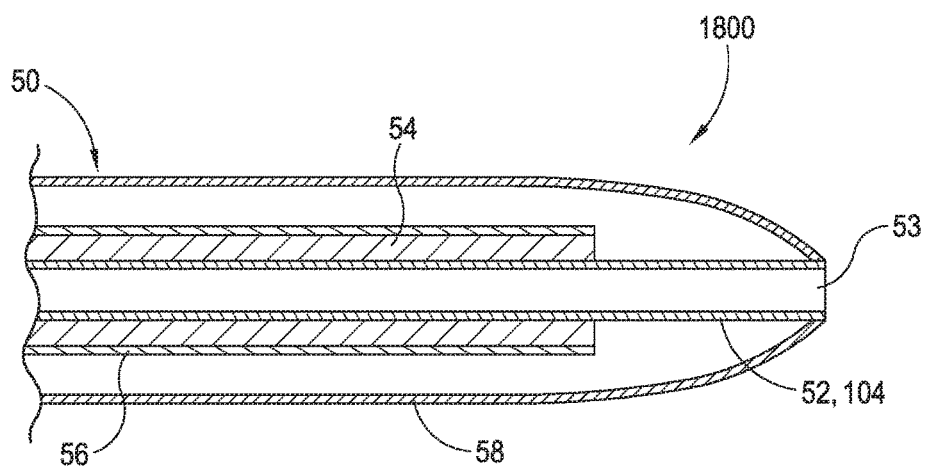
FIG. 18A is a schematic side-sectional view of the distal region of an embodiment of the microwave treatment device of FIG. 5 configured for delivery over a guide wire.
Figure 18B:
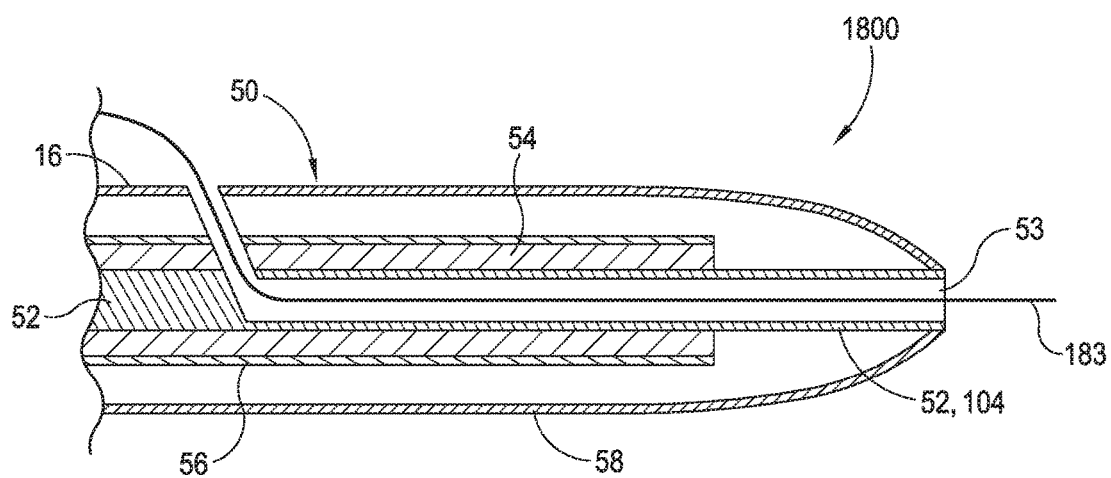
FIG. 18B is a schematic side-sectional view of the distal region of an embodiment of the microwave treatment device of FIG. 5 configured for rapid exchange delivery.

It may be desirable for the microwave system 10 to comprise an intravascular treatment device 12 configured for delivery over a guide wire. In any of the previously described embodiments, the coaxial cable 50 and coaxial antenna 100 may be modified such that the inner conductor 52 comprises a tubular inner conductor with a guide wire lumen (e.g., a coiled tube, a braided metal tube, or a flexible polymer tube coated with a conductive material, such as silver). For example, FIG. 18A illustrates an alternative embodiment of the microwave system of FIG. 7 having an antenna 1800 wherein the inner conductor 52 comprises a tubular inner conductor having a guide wire lumen 53. In the embodiment illustrated in FIG. 18A, the guide wire lumen 53 extends completely through the shaft 16 from the proximal opening of the shaft 16 at an adaptor (e.g., at the handle 200 shown in FIG. 5) to the distal opening of the shaft 16 in an over-the-wire (OTW) configuration, whereas in the embodiment illustrated in FIG. 18B, a guide wire 183 and the guide wire lumen 53 extend through only a portion of the shaft 16 in a rapid exchange (RX) configuration. Although the proximal end of the guide wire lumen 53 is shown in FIG. 18B extending through the sidewall of the shaft 16 at the distal region 20, in other embodiments, the proximal end of the guide wire lumen 53 can be accessible anywhere between the proximal and distal ends of the shaft 16. The guide wire lumen 53 shown in FIGS. 18A and 18B, or variations thereof, may be included in various embodiments described herein to facilitate navigation through the vasculature. Suitable OTW and RX guide wire configurations are disclosed in U.S. Pat. No. 5,545,134, filed Oct. 27, 1994, U.S. Pat. No. 5,782,760, filed May 23, 1995, U.S. Patent App. Publication No. US 2003/0040769, filed Aug. 23, 2001, and U.S. Patent App. Publication No. US 2008/0171979, filed Oct. 17, 2006, each of which is incorporated herein by reference in its entirety.

6. Inner Conductors with Dynamically Variable Exposed Length

When utilizing a coaxial antenna, it may be desirable to provide the inner conductor 52 with a dynamically variable exposed length in order to better match the antenna to the surrounding media (i.e., blood and tissue). Media matching depends on multiple factors, including electrical characteristics of the media (e.g., dielectric properties), frequency of the microwave signal, and power of the microwave signal, as well as geometrical parameters of the radiating element 106 of the antenna. Dynamically varying the exposed length of the inner conductor 52 dynamically varies the geometrical parameters of the radiating element 106, which may be utilized to facilitate better media matching.

Figure 19A:
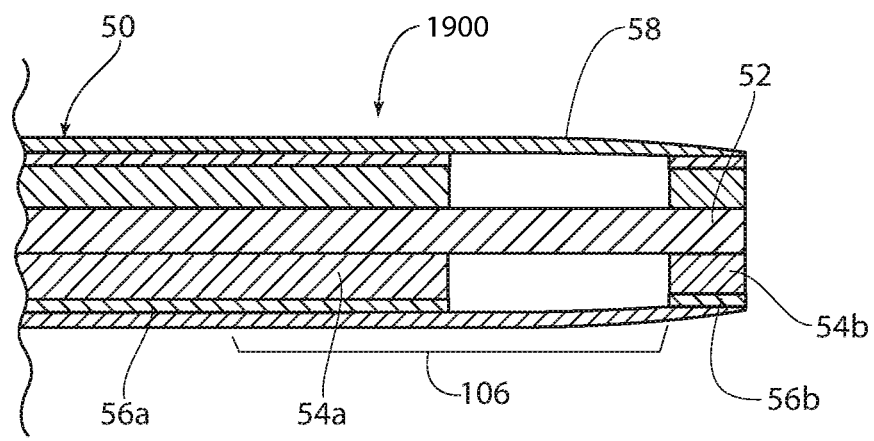
FIGS. 19A and 19B are schematic side-sectional views of the distal region of an embodiment of the microwave treatment device of FIG. 5 illustrating dynamic variation of the coaxial antenna's radiating element.
Figure 19B:
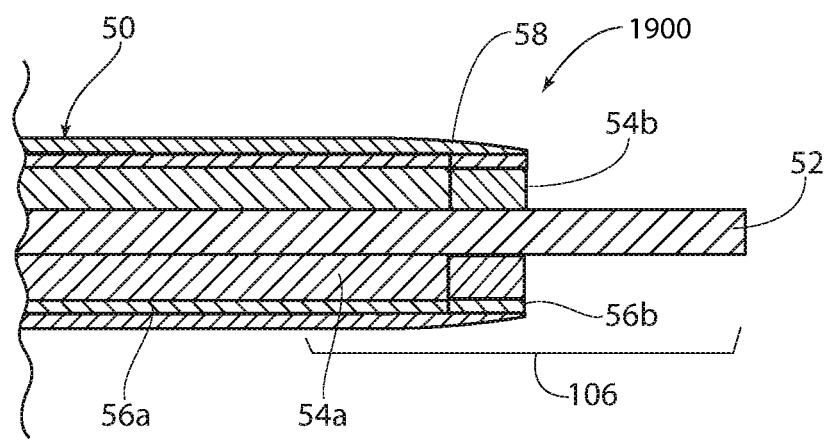

Referring now to FIGS. 19A and 19B, in one embodiment, a coaxial antenna 1900 may comprise an adjustable gap for dynamically varying the exposed length of the inner conductor 52. As seen in FIG. 19A, the distal region of outer conductor 56 may comprise a first outer conductor 56a and a second outer conductor 56b spaced longitudinally from the first outer conductor 56a. Likewise the (dielectric) insulation 54 comprises a first insulation 54a and a second insulation 54b spaced longitudinally from the first insulation 54a. The outer sheath 58 is attached to the second outer conductor 56b, but may freely slide relative to first outer conductor 56a.

In FIG. 19A, radiating element 106 of antenna 1900 comprises the exposed portion of inner conductor 52 positioned between the first and second outer conductors. As seen in FIG. 19B, proximal retraction of outer sheath 58 proximally retracts the second outer conductor 56b and the second insulation 54b relative to the inner conductor 52, thereby dynamically altering the radiating element 106 of the antenna 1900. As will be apparent, in an alternative embodiment, the microwave system of FIGS. 19A and 19B may be modified such that the inner conductor 52 comprises a tubular inner conductor having a guide wire lumen to facilitate over-the-wire delivery of the treatment device 12. The microwave system may alternatively be modified for RX delivery of the treatment device 12.

Figure 20:
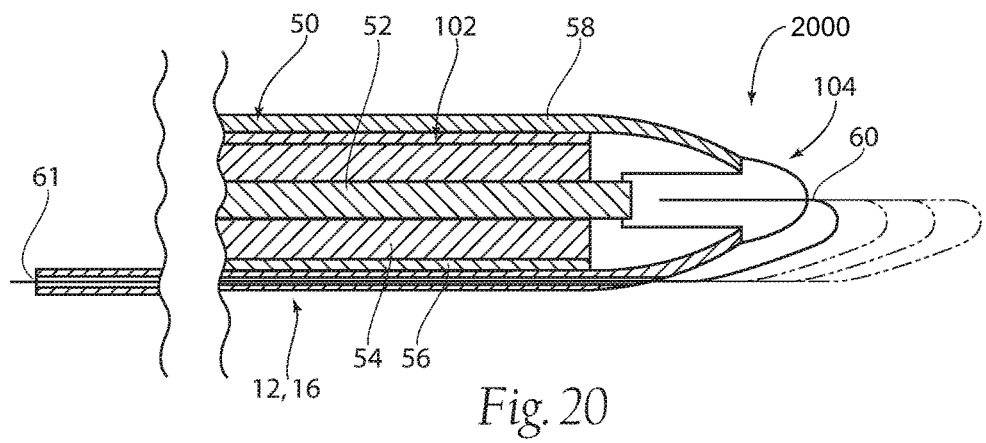
FIG. 20 is schematic side-sectional view of the distal region of an alternative embodiment of the microwave treatment device of FIGS. 19A and 19B configured for dynamic variation of the coaxial antenna's radiating element.

FIG. 20 illustrates another embodiment of an antenna 2000 having an inner conductor 52 with a dynamically variable exposed length distal region 104. In FIG. 20, the exposed length along the distal region 104 of the inner conductor 52 includes a conductive wire loop 60 that loops back and extends within a lumen 61 through an elongated shaft 16 of an intravascular treatment device 12. As illustrated by dotted lines in FIG. 20, the medical practitioner may dynamically extend and retract the wire loop 60 to dynamically vary the exposed length of the inner conductor 52.

Figure 21A:
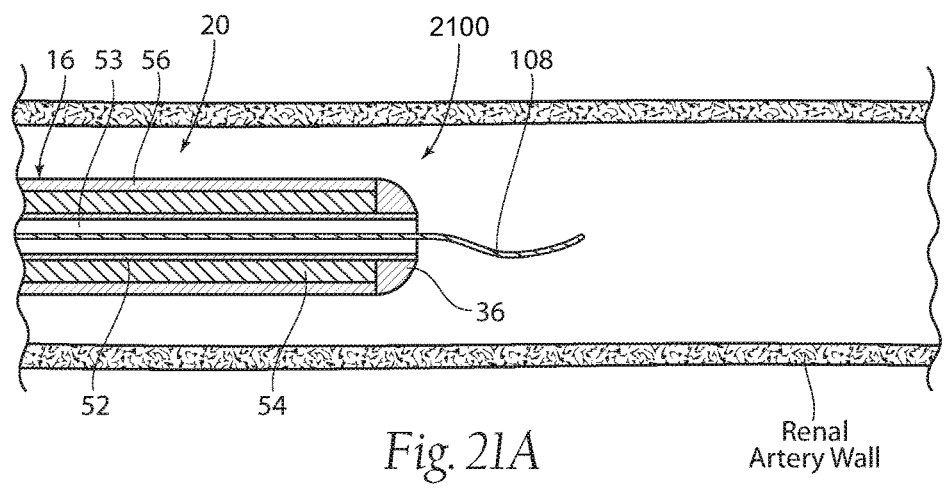
FIGS. 21A and 21B are schematic side-sectional views of the distal region of another alternative embodiment of the microwave treatment device of FIGS. 19A and 19B configured for dynamic variation of the coaxial antenna's radiating element and for over-the-wire delivery.
Figure 21B:
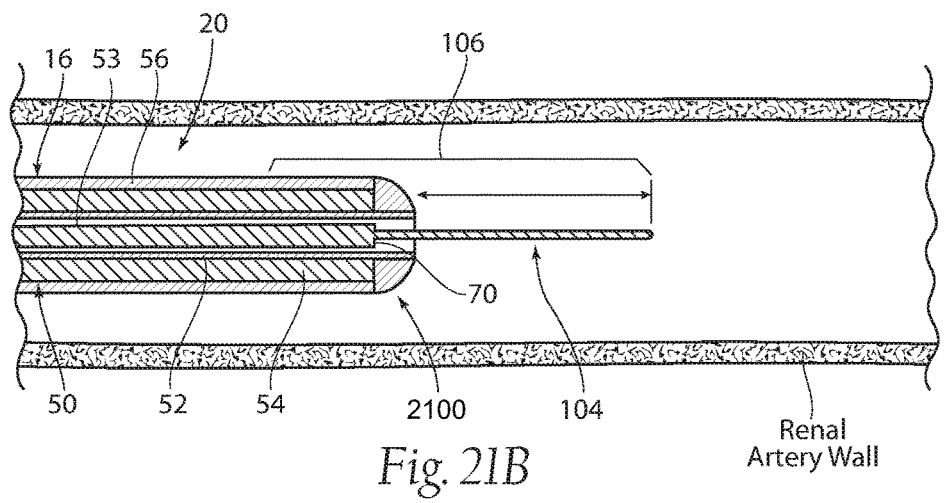

FIGS. 21A and 21B illustrate an over-the-wire embodiment of a microwave system having an inner conductor 52 with a dynamically variable exposed length. As seen in FIG. 21A, the distal end region 20 of the elongated shaft 16 having a coaxial antenna 2100 with tubular inner conductor 52 having a guide wire lumen 53 may be advanced over a guide wire 108 into the renal artery. As seen in FIG. 21B, the guide wire 108 then may be removed and replaced with a radiator 70 that is electrically coupled to the tubular inner conductor 52. The radiator 70 may, for example, comprise protrusions that contact the inner wall of the inner conductor 52 to electrically couple to the tubular inner conductor 52.

The radiator 70 extends beyond the distal end region 20 of the elongated shaft 16 to form the exposed distal region 104 of the inner conductor 52, thereby forming a portion of the radiating element 106 of the antenna 2100 during microwave irradiation of the renal nerves. The length of the exposed distal region 104 of inner conductor 52 may be varied by dynamically varying how far the radiator 70 extends beyond distal end region 20 of elongated shaft 16.

7. Active Cooling

Figure 22A:
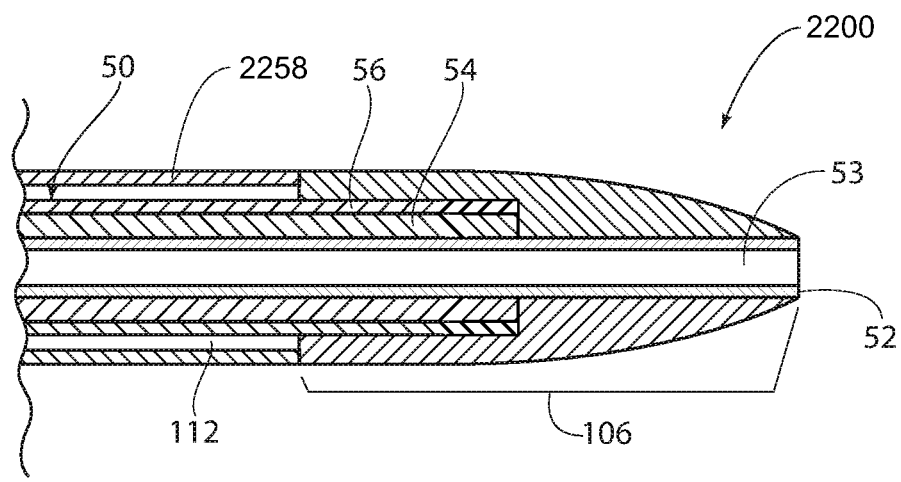
FIGS. 22A and 22B are schematic side-sectional views of the distal regions of embodiments of the microwave treatment device of FIG. 5 configured for active cooling.
Figure 22B:
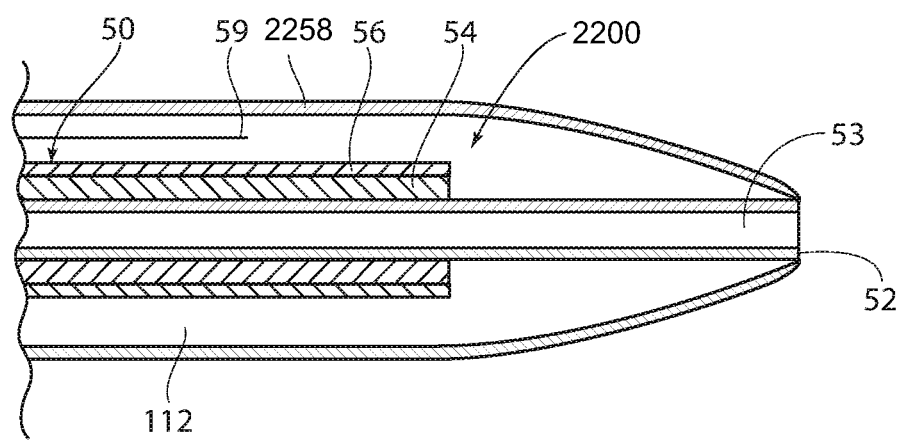

In addition to the passive cooling provided by blood flow, active cooling may be provided in the vicinity of the microwave transmission element via a coolant (e.g., a circulating coolant). For example, as seen in FIG. 22A, a coolant 112 may be introduced into an annular space between the coaxial cable 50 and dielectric or insulator 2258. As seen in FIG. 22B, the annular space may extend over a coaxial antenna 2200. Optionally, the coolant may be circulated to enhance heat transfer. Optionally, a temperature sensor, such as a thermistor or thermocouple 59, may be positioned within the coolant in the vicinity of the radiating element of the antenna 2200 to monitor temperature. Temperature data collected with the temperature sensor may be utilized in a feedback loop to control or alter delivery of the microwave field and/or the coolant in response to the measured temperature (e.g., to maintain the temperature within a desired range).

Additionally or alternatively, the inner layers of an artery may be spared from heat if microwave energy is delivered in pulses. During pauses of energy delivery, blood will flow away from the area of energy application and be replaced by colder blood. At the same time tissues surrounding the inner lumen of the artery will continue to accumulate heat leading to the desired targeted tissue destruction. Pulsed delivery of microwave energy can be achieved by setting the duty cycle of the microwave energy generator. The thermal inertia of the targeted tissues will ensure the desired build up of heat while sparing the inner lumen of the blood vessel.

8. Directed Application of a Microwave Field

The specific embodiments described above provide toroidal-shaped, omni-directional emission of microwaves from a microwave transmission element 24 (i.e., from the radiating element 106 of coaxial antenna 100). While such an omni-directional microwave energy deposition delivered intravascularly may desirably provide a circumferential treatment about the renal artery, it may be desirable under certain circumstances to target a specific non-circumferential area (e.g., to more narrowly direct application of the microwave energy deposition to specific target renal nerves). Thus, a microwave transmission element 24 may include shielding or other means for directional application of microwave energy.

Figure 23A:
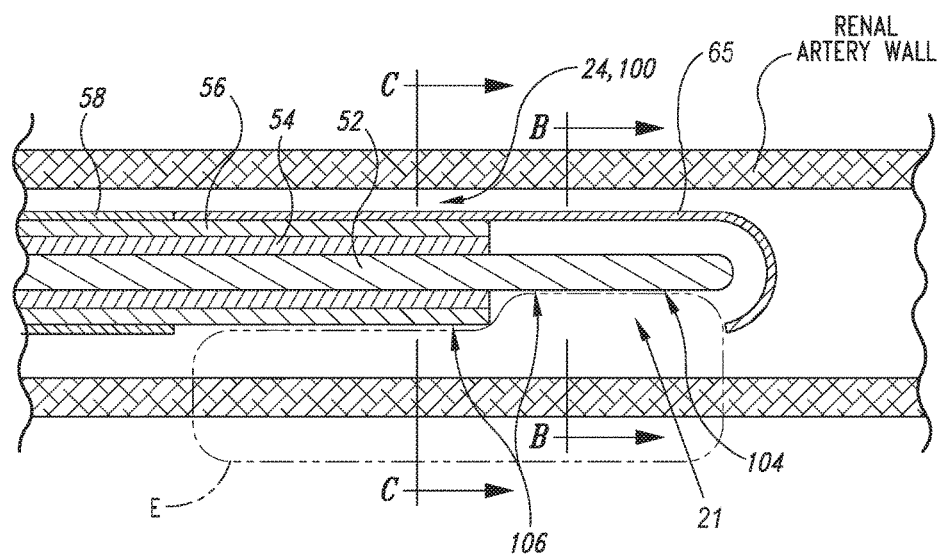
FIG. 23A is a schematic side-sectional view of the distal region of an embodiment of a microwave treatment device having a shielding component.
Figure 23B:
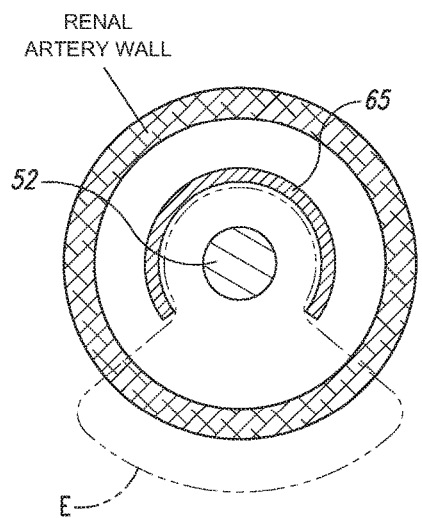
FIGS. 23B and 23C are cross-sectional views of the microwave treatment device of FIG. 23A.
Figure 23C:
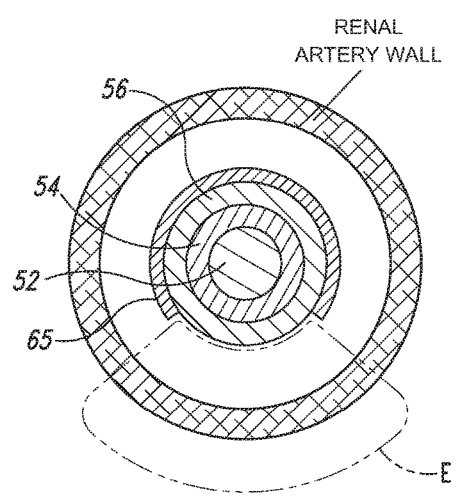

For example, FIG. 23A illustrates a shielding 65 substantially surrounding the radiating element 106 of the coaxial antenna 100. FIGS. 23B and 23C are cross-sectional views of the antenna 100 along lines B-B and C-C, respectively. Referring to FIGS. 23A-23C, the shielding 65 includes a window 21 through which the microwave emissions E may be directed. The window 21 can take up various proportions of the circumference of the shielding 65. For example, in one embodiment, the window 21 comprises approximately 30% of the circumference of the shielding 65 over the length of the emitting portion of the antenna 100. In further embodiments, the window 21 can comprise more or less of the circumference of the shielding 65 and can extend only part of the length of the emitting portion of the antenna 100. In some embodiments, it may be desirable for the shielding 65 to possess reflective properties such that a substantial portion of the omni-directional field that encounters the shielding 65 is redirected through the window 21. In further embodiments, the shielding 65 can include more than one window (e.g., multiple longitudinally offset windows facing opposite directions, or a helical window, etc.). The lesion geometry will accordingly match the window geometry.

Figure 23D:
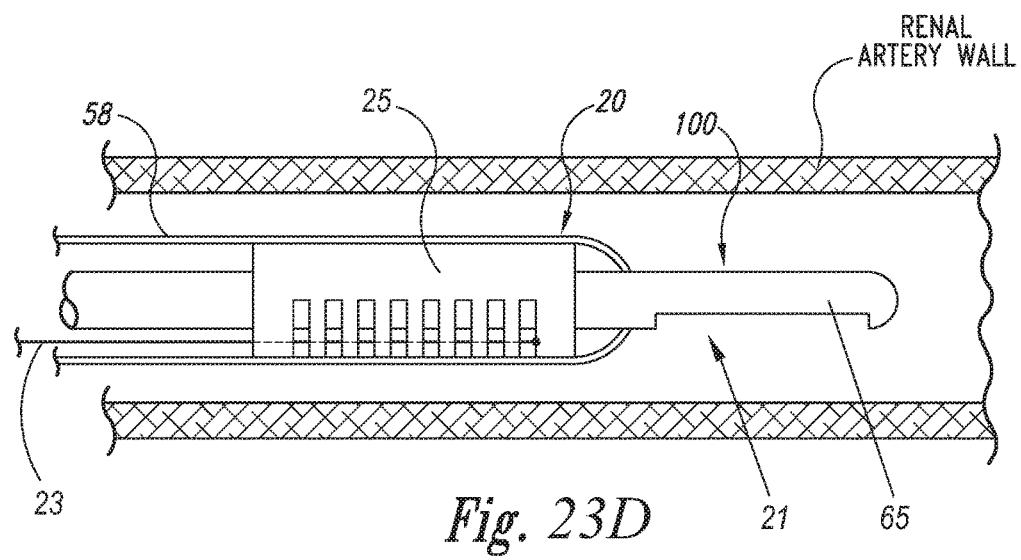
FIGS. 23D and 23E are schematic side views of the distal region of an embodiment of a microwave treatment device having a shielding component and deflection capabilities.
Figure 23E:
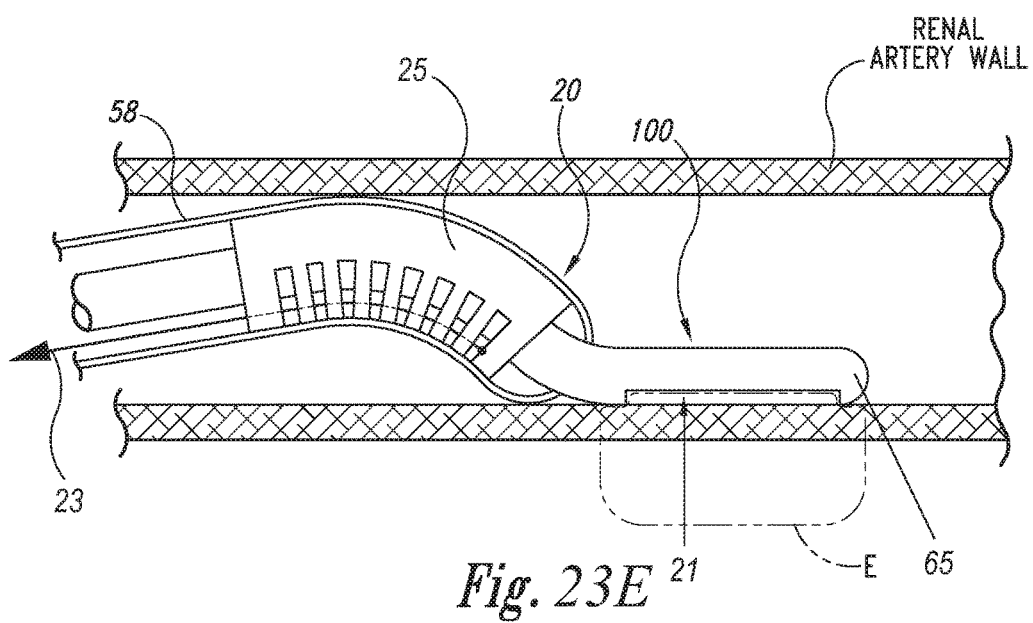

In some embodiments, it may also be desirable for the elongated shaft 16 (FIG. 5) to have deflection capability at or near its distal region 20 proximal of the antenna 100 to facilitate positioning of the shielding window 21 within the renal artery. For example, as illustrated in FIGS. 23D and 23E, deflection capability may be provided by a control wire 23 running through the catheter from the handle to or near the distal region 20 proximal of the antenna 100, where the catheter includes a flexibly biased structure such as a laser cut tube 25. When the control wire 23 is pulled or pushed by an actuator in the handle (not shown), the flexibly biased structure is deflected in the flexibly biased direction.

In one embodiment, pulling or pushing the control wire 23 can cause the distal region 20 to deflect in the direction of the window 21 to facilitate positioning of the window 21 in substantial contact with the vessel wall (as illustrated in FIG. 23E). In another embodiment, pulling or pushing the control wire 23 can cause the catheter to deflect in a direction opposite that of the window 21 to ensure that there is sufficient space between the window 21 and targeted area of the vessel wall to allow for blood flow to cool non-target intima/media tissue. Other embodiments disclosed herein (e.g., balloon-centering embodiments), can similarly employ an elongated shaft 16 having deflection capabilities to control positioning of the antenna 100 in the renal artery.

III. Conclusion

Although the specific embodiments of a microwave system have been described with a feed line comprising a coaxial cable and a microwave transmission element comprising a coaxial antenna, it should be understood that any alternative feed lines and microwave transmission elements may be utilized. For example, a feed line may comprise a parallel wire. Likewise, a microwave transmission element may, for example, comprise a waveguide or an alternative type of antenna, such as a patch antenna, a slot antenna, another form of dipole antenna, a Yagi-Uda antenna, a parabolic antenna, etc.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Where the context permits, singular or plural terms may also include the plural or singular term, respectively. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A method for treatment of a human patient via renal denervation, the method comprising:
    intravascularly positioning a catheter having a microwave transmitting element within a renal artery of the patient, wherein the microwave transmitting element is within an expandable centering element;
    centering the microwave transmitting element within the renal artery via the expandable centering element,
    wherein the expandable centering element is transformable between a low-profile delivery configuration and an expanded configuration within the renal artery, and further wherein, in the expanded configuration, the expandable centering element is sized and shaped to occlude blood flow through the renal artery;
    omni-directionally radiating microwave energy from a microwave generator external to the patient via the microwave transmitting element to at least partially ablate renal nerves along the renal artery of the patient, wherein the microwave energy is delivered omni-directionally in a plane relatively perpendicular to a longitudinal axis of the renal artery via the microwave transmitting element; and
    actively cooling the microwave transmitting element while radiating the microwave energy to the target renal nerves.

2. The method of claim 1 wherein omni-directionally radiating microwave energy via the microwave transmitting element to at least partially ablate the renal nerves comprises dielectrically heating the renal nerves.

3. The method of claim 2 wherein dielectrically heating the renal nerves comprises inducing necrosis in the renal nerves.

4. The method of claim 1 wherein intravascularly positioning a catheter having a microwave transmitting element comprises intravascularly positioning a catheter having a microwave antenna.

5. The method of claim 4 wherein intravascularly positioning a catheter having a microwave antenna comprises positioning a catheter having a coaxial antenna.

6. The method of claim 5 wherein the coaxial antenna includes a radiating element, and wherein radiating microwave energy from a microwave generator external to the patient via the microwave transmitting element comprises dynamically varying a length of the radiating element.

7. The method of claim 5 wherein the coaxial antenna includes a radiating element, and wherein radiating the microwave energy from a microwave generator external to the patient via the microwave transmitting element further comprises shielding a portion of the radiating element of the coaxial antenna to preferentially direct the radiated microwave energy.

8. The method of claim 1 wherein omni-directionally radiating microwave energy from a microwave generator external to the patient via the microwave transmitting element comprises transferring the microwave energy through a coaxial cable to the coaxial antenna.

9. The method of claim 1 wherein intravascularly positioning a catheter having a microwave transmitting element within the renal artery comprises advancing the catheter to the renal artery over a guide wire via an intravascular path.

10. The method of claim 1 wherein actively cooling the microwave transmitting element comprises circulating a coolant within the expandable element surrounding the microwave transmitting element.

11. The method of claim 1, further comprising monitoring a temperature of the microwave transmitting element and/or tissue of the patient while radiating microwave energy.

12. The method of claim 11, further comprising altering the active cooling or the microwave energy in response to the monitored temperature.

13. The method of claim 1, further comprising monitoring a temperature of the microwave transmitting element.

14. The method of claim 1 wherein at least partially ablating the renal nerves comprises at least partially denervating a kidney of the patient.

15. The method of claim 1 wherein at least partially ablating the renal nerves comprises thermally ablating the renal nerves from within the renal blood vessel.

* * * * *